United States Patent [19]
Barnett et al.

[11] Patent Number: 5,274,087
[45] Date of Patent: Dec. 28, 1993

[54] CDNA CODING FOR CARCINOEMBRYONIC ANTIGEN (CEA)

[75] Inventors: Thomas R. Barnett, East Haven; James J. Elting, Madison; Michael E. Kamarck, Bethany, all of Conn.

[73] Assignee: Molecular Diagnostics, Inc., West Haven, Conn.

[21] Appl. No.: 876,821

[22] Filed: Apr. 29, 1992

Related U.S. Application Data

[63] Continuation of Ser. No. 231,741, Aug. 12, 1988, abandoned, which is a continuation-in-part of Ser. No. 60,031, Jun. 19, 1987, abandoned, which is a continuation-in-part of Ser. No. 16,683, Feb. 19, 1987, abandoned, which is a continuation-in-part of Ser. No. 896,361, Aug. 13, 1986, abandoned.

[51] Int. Cl.$^5$ .............. C07H 15/12; C07H 21/04; C12N 15/00
[52] U.S. Cl. .............. 536/23.5; 435/6; 435/172.3; 435/320.1; 536/23.5; 536/24.3; 536/24.31; 935/11; 935/27
[58] Field of Search .............. 435/91, 172.3, 240.1, 435/240.4, 252.3, 252.33, 254.34, 6, 320.1; 536/27, 24.3, 24.31, 24.5; 935/11, 27

[56] References Cited

U.S. PATENT DOCUMENTS 4,180,499 12/1979 Hansen .............. 530/417
4,228,236 10/1980 Jakstys et al. .............. 435/1

OTHER PUBLICATIONS

Maniatis et. al. (1982) Molecular Cloning, Cold Spring Harbor Press, N.Y.
Oikawa et al. (1987), Biochemical & Biophysical Research Com., vol. 142, No. 2, pp. 511–518.
Paxton et al. (1987), Proc. Natl. Acad. Sci., vol. 84, pp. 920–924.
Thompson et al. (1987), Proc. Natl. Acad. Sci, vol. 84, pp. 2965–2969.
Zimmerman et al. (1987), Proc. Natl. Acad. Sci, vol. 84, pp. 2960–2964.
Young et al. (1983), Proc. Natl. Acad. Sci, vol. 88, pp. 1194–1198.
Glassman et al. (1978), Biochem. Biophys. Res. Com., vol. 85, pp. 209–216.
Engvall et al. (1978), Proc. Natl. Acad. Sci. vol. 75, pp. 1670–1674.
Rogers et al. (1983),. Biochimica et Biophysica Act., vol. 695, pp. 277–249.
Zimmerman et al. (1983), Annals NY Acad. Sci, vol. , pp. 21–30.
Suggs et al. (1981), Proc. Natl. Sci, vol. 78, pp. 6613–6617.
Paxton et al. (1985), Abst. Int. Soc. Oncodev. Biol. Med XIII, No. A14, p. 47.
Chemical Abstracts, vol. 101, No. 21, Nov. 19th 1984, p. 189, abstract No. 185160x, Columbus, Ohio, US; J. E. Shively et al: "Structural studies on carcinoembryonic antigen: molecular cloning of carcinoembryonic antigen using mixed synthetic oligonucleotide probes", & Proc. Cancer Res. Ther. 1984, 29 (Markers Colonic Cell Differ.), 147–57.
Chemical Abstracts, vol. 105, No. 7, Aug. 19th 1986, p. 162, abstract No. 55557d, Columbus, Ohio, US; T. Higashide: "Studies on DNA methylation and gene expression. With special reference to the oncodevelopmental protein genes", & Sapporo Igaku Zasshi 1986, 55(2), 79–91.

(List continued on next page.)

Primary Examiner—Jacqueline Stone
Assistant Examiner—Brian R. Stanton
Attorney, Agent, or Firm—Sprung Horn Kramer & Woods

[57] ABSTRACT

Nucleic acid sequences are disclosed that encode carcinoembryonic antigens (CEAs) as are replicable recombinant cloning vehicles containing DNA that encodes CEA proteins.

8 Claims, 12 Drawing Sheets

OTHER PUBLICATIONS

Chemical Abstracts, vol. 100, No. 23, Jun. 4th 1984, p. 216, abstract No. 187487n, Columbus, Ohio, US; W Zimmerman et al: "Characterization of messenger RNA specific for carcinoembryonic antigen", & Ann. NY. Y. Acad. Sci. 1983, 417 (Oncodev. Biol. Med.), 21-30.

Proceedings of the National Academy of Sciences of the USA, vol. 84, No. 16, Aug. 1987, pp. 5350-5354; M. E. Kamarck et al: "Carcinoembryonic antigen family: Expression in a mouse L-cell transfectant and characterization of a partial cDNA in bacteriophage lambdagell".

Proceedings of the National Academy of Sciences of the USA, vol. 84, No. 9, May 1987, pp. 2960-2964; W. Zimmerman et al: "Isolation and characterization of cDNA clones encoding the human carcinoembryonic antigen reveal a highly conserved repeating structure".

Proceedings of the National Academy of Sciences of the USA, vol. 84, No. 9, May 1987, pp. 2965-2969; J. A. Thompson et al: "Molecular cloning of a gene belonging to the carcinoembroyonic antigen gene family and discussion of a domain model".

```
             10              20              30              40
              *               *               *               *
G GGT TTA CAC AAC CAC CAC CCC ATC AAA CCC TTC ATC ACC
  Gly Leu His Asn His His Pro Ile Lys Pro Phe Ile Thr 50              60              70              80
          *               *               *               *
AGC AAC AAC TCC AAC CCC GTG GAG GAT GAG GAT GCT GTA GCC
Ser Asn Asn Ser Asn Pro Val Glu Asp Glu Asp Ala Val Ala 90             100             110             120
          *               *               *               *
TTA ACC TGT GAA CCT GAG ATT CAG AAC ACA ACC TAC CTG TGG
Leu Thr Cys Glu Pro Glu Ile Gln Asn Thr Thr Tyr Leu Trp 130             140             150             160
          *               *               *               *
TGG GTA AAT AAT CAG AGC CTC CCG GTC AGT CCC AGG CTG CAG
Trp Val Asn Asn Gln Ser Leu Pro Val Ser Pro Arg Leu Gln 170             180             190             200
          *               *               *               *
CTG TCC AAT GAC AAC AGG ACC CTC ACT CTA CTC AGT GTC ACA
Leu Ser Asn Asp Asn Arg Thr Leu Thr Leu Leu Ser Val Thr 210             220             230             240             250
    *               *               *               *               *
AGG AAT GAT GTA GGA CCC TAT GAG TGT GGA ATC CAG AAC GAA
Arg Asn Asp Val Gly Pro Tyr Glu Cys Gly Ile Gln Asn Glu 260             270             280             290
          *               *               *               *
TTA AGT GTT GAC CAC AGC GAC CCA GTC ATC CTG AAT GTC CTC
Leu Ser Val Asp His Ser Asp Pro Val Ile Leu Asn Val Leu 300             310             320             330
          *               *               *               *
TAT GGC CCA GAC GAC CCC ACC ATT TCC CCC TCA TAC ACC TAT
Tyr Gly Pro Asp Asp Pro Thr Ile Ser Pro Ser Tyr Thr Tyr 340             350             360             370
          *               *               *               *
TAC CGT CCA GGG GTG AAC CTC AGC CTC TCC TGC CAT GCA GCC
Tyr Arg Pro Gly Val Asn Leu Ser Leu Ser Cys His Ala Ala 380             390             400             410
          *               *               *               *
TCT AAC CCA CCT GCA CAG TAT TCT TGG CTG ATT GAT GGG AAC
Ser Asn Pro Pro Ala Gln Tyr Ser Trp Leu Ile Asp Gly Asn 420             430             440             450             460
    *               *               *               *               *
ATC CAG CAA CAC ACA CAA GAG CTC TTT ATC TCC AAC ATC ACT
Ile Gln Gln His Thr Gln Glu Leu Phe Ile Ser Asn Ile Thr
```

FIG. 1a

```
        470             480             490             500
         *               *               *               *
GAG AAG AAC AGC GGA CTC TAT ACC TGC CAG GCC AAT AAC TCA
Glu Lys Asn Ser Gly Leu Tyr Thr Cys Gln Ala Asn Asn Ser
      510             520             530             540
       *               *               *               *
GCC AGT GGC CAC AGC AGG ACT ACA GTC AAG ACA ATC ACA GTC
Ala Ser Gly His Ser Arg Thr Thr Val Lys Thr Ile Thr Val
    550             560             570             580
     *               *               *               *
TCT GCG GAC GTG CCC AAG CCC TCC ATC TCC AGC AAC AAC TCC
Ser Ala Asp Val Pro Lys Pro Ser Ile Ser Ser Asn Asn Ser
  590             600             610             620
   *               *               *               *
AAA CCC GTG GAG GAC AAG GAT GCT GTG GCC TTC CAC TGT GAA
Lys Pro Val Glu Asp Lys Asp Ala Val Ala Phe His Cys Glu
 630             640             650             660             670
  *               *               *               *               *
CCT GAG GCT CAG AAG ACA ACC TAC CTG TGG TGG GTA AAT GGT
Pro Glu Ala Gln Asn Thr Thr Tyr Leu Trp Trp Val Asn Gly
      680             690             700             710
       *               *               *               *
CAG AGC CTC CCA GTC AGT CCC AGG CTG CAG CTG TCC AAT GGC
Gln Ser Leu Pro Val Ser Pro Arg Leu Gln Leu Ser Asn Gly
        720             730             740             750
         *               *               *               *
AAC AGG ACC CTC ACT CTA TTC AAT GTC ACA AGA AAT GAC GCA
Asn Arg Thr Leu Thr Leu Phe Asn Val Thr Arg Asn Asp Ala
      760             770             780             790
       *               *               *               *
AGA GCC TAT GTA TGT GGA ATC CAG AAC TCA GTG AGT GCA AAC
Arg Ala Tyr Val Cys Gly Ile Gln Asn Ser Val Ser Ala Asn
    800             810             820             830
     *               *               *               *
CGC AGT GAC CCA GTC ACC CTG GAT GTC CTC TAT GGG CCG GAC
Arg Ser Asp Pro Val Thr Leu Asp Val Leu Tyr Gly Pro Asp
  840             850             860
   *               *               *
ACC CCC ATC ATT TCC CCC CCC CC
Thr Pro Ile Ile Ser Pro Pro
```

FIG. 1b

```
            10                  20                  30              40
             *                   *                   *               *
C  ACC ATG GAG TCT CCC TCG GCC CCT CTC CAC AGA TGG TGC
   Met Glu Ser Pro Ser Ala Pro Leu His Arg Trp Cys
                50                  60                  70
                 *                   *                   *
ATC CCC TGG CAG AGG CTC CTG CTC ACA GCC TCA CTT CTA
Ile Pro Trp Gln Arg Leu Leu Leu Thr Ala Ser Leu Leu 80                  90                  100                 110
  *                   *                    *                   *
ACC TTC TGG AAC CCG CCC ACC ACT GCC AAG CTC ACT ATT
Thr Phe Trp Asn Pro Pro Thr Thr Ala Lys Leu Thr Ile
                                         1   2   3

120                  130                 140                 150
  *                    *                   *                   *
GAA TCC ACG CCG TTC AAT GTC GCA GAG GGG AAG GAG GTG
Glu Ser Thr Pro Phe Asn Val Ala Glu Gly Lys Glu Val 160                 170                 180                 190
    *                   *                   *                   *
CTT CTA CTT GTC CAC AAT CTG CCC CAG CAT CTT TTT GGC
Leu Leu Leu Val His Asn Leu Pro Gln His Leu Phe Gly 200                 210                 220                 230
        *                   *                   *                   *
TAC AGC TGG TAC AAA GGT GAA AGA GTG GAT GGC AAC CGT
Tyr Ser Trp Tyr Lys Gly Glu Arg Val Asp Gly Asn Arg 240                 250                 260                 270
        *                   *                   *                   *
CAA ATT ATA GGA TAT GTA ATA GGA ACT CAA CAA GCT ACC
Gln Ile Ile Gly Tyr Val Ile Gly Thr Gln Gln Ala Thr 280                 290                 300                 310
        *                   *                   *                   *
CCA GGG CCC GCA TAC AGT GGT CGA GAG ATA ATA TAC CCC
Pro Gly Pro Ala Tyr Ser Gly Arg Glu Ile Ile Tyr Pro 320                 330                 340                 350
        *                   *                   *                   *
AAT GCA TCC CTG CTG ATC CAG AAC ATC ATC CAG AAT GAC
Asn Ala Ser Leu Leu Ile Gln Asn Ile Ile Gln Asn Asp 360                 370                 380                 390
        *                   *                   *                   *
ACA GGA TTC TAC ACC CTA CAC GTC ATA AAG TCA GAT CTT
Thr Gly Phe Tyr Thr Leu His Val Ile Lys Ser Asp Leu
```

FIG. 5a

```
            400               410               420               430
             *                 *                 *                 *
GTG AAT GAA GAA GCA ACT GGC CAG TTC CGG GTA TAC CCG
Val Asn Glu Glu Ala Thr Gly Gln Phe Arg Val Tyr Pro 440               450               460
           *                 *                 *
GAG CTG CCC AAG CCC TCC ATC TCC AGC AAC AAC TCC AAA
Glu Leu Pro Lys Pro Ser Ile Ser Ser Asn Asn Ser Lys 470               480               490               500
  *                 *                 *                 *
 CCC GTG GAG GAC AAG GAT GCT GTG GCC TTC ACC TGT GAA
 Pro Val Glu Asp Lys Asp Ala Val Ala Phe Thr Cys Glu 510               520               530               540
  *                 *                 *                 *
CCT GAG ACT CAG GAC GCA ACC TAC CTG TGG TGG GTA AAC
Pro Glu Thr Gln Asp Ala Thr Tyr Leu Trp Trp Val Asn 550               560               570               580
     *                 *                 *                 *
AAT CAG AGC CTC CCG GTC AGT CCC AGG CTG CAG CTG TCC
Asn Gln Ser Leu Pro Val Ser Pro Arg Leu Gln Leu Ser 590               600               610               620
    *                 *                 *                 *
AAT GGC AAC AGG ACC CTC ACT CTA TTC AAT GTC ACA AGA
Asn Gly Asn Arg Thr Leu Thr Leu Phe Asn Val Thr Arg 630               640               650               660
     *                 *                 *                 *
AAT GAA CAA GCA AGC TAC AAA TGT GAA ACC CAG AAC CCA
Asn Glu Gln Ala Ser Tyr Lys Cys Glu Thr Gln Asn Pro 670               680               690               700
       *                 *                 *                 *
GTG AGT GCC AGG CGC AGT GAT TCA GTC ATC CTG AAT GTC
Val Ser Ala Arg Arg Ser Asp Ser Val Ile Leu Asn Val 710               720               730               740
           *                 *                 *                 *
CTC TAT GGC CCG GAT GCC CCC ACC ATT TCC CCT CTA AAC
Leu Tyr Gly Pro Asp Ala Pro Thr Ile Ser Pro Leu Asn 750               760               770               780
           *                 *                 *                 *
ACA TCT TAC AGA TCA GGG GAA AAT CTG AAC CTC TCC TGC
Thr Ser Tyr Arg Ser Gly Glu Asn Leu Asn Leu Ser Cys 790               800               810               820
           *                 *                 *                 *
CAC GCA GCC TCT AAC CCA CCT GCA CAG TAC TCT TGG TTT
His Ala Ala Ser Asn Pro Pro Ala Gln Tyr Ser Trp Phe
```

FIG. 5b

```
              830              840              850
               *                *                *
GTC AAT GGG ACT TTC CAG CAA TCC ACC CAA GAG CTC TTT
Val Asn Gly Thr Phe Gln Gln Ser Thr Gln Glu Leu Phe 860              870              880              890
    *                *                *                *
 ATC CCC AAC ATC ACT GTG AAT AAT AGT GGA TCC TAT ACG
 Ile Pro Asn Ile Thr Val Asn Asn Ser Gly Ser Tyr Thr 900              910              920              930
 *                *                *                *
TGC CAA GCC CAT AAC TCA GAC ACT GGC CTC AAT AGG ACC
Cys Gln Ala His Asn Ser Asp Thr Gly Leu Asn Arg Thr 940              950              960              970
  *                *                *                *
ACA GTC ACG ACG ATC ACA GTC TAT GCA GAG CCA CCC AAA
Thr Val Thr Thr Ile Thr Val Tyr Ala Glu Pro Pro Lys 980              990              1000             1010
    *                *                *                *
CCC TTC ATC ACC AGC AAC AAC TCC AAC CCC GTG GAG GAT
Pro Phe Ile Thr Ser Asn Asn Ser Asn Pro Val Glu Asp 1020             1030             1040             1050
    *                *                *                *
GAG GAT GCT GTA GCC TTA ACC TGT GAA CCT GAG ATT CAG
Glu Asp Ala Val Ala Leu Thr Cys Glu Pro Glu Ile Gln 1060             1070             1080             1090
    *                *                *                *
AAC ACA ACC TAC CTG TGG TGG GTA AAT AAT CAG AGC CTC
Asn Thr Thr Tyr Leu Trp Trp Val Asn Asn Gln Ser Leu 1100             1110             1120             1130
    *                *                *                *
CCG GTC AGT CCC AGG CTG CAG CTG TCC AAT GAC AAC AGG
Pro Val Ser Pro Arg Leu Gln Leu Ser Asn Asp Asn Arg 1140             1150             1160             1170
    *                *                *                *
ACC CTC ACT CTA CTC AGT GTC ACA AGG AAT GAT GTA GGA
Thr Leu Thr Leu Leu Ser Val Thr Arg Asn Asp Val Gly 1180             1190             1200             1210
    *                *                *                *
CCC TAT GAG TGT GGA ATC CAG AAC GAA TTA AGT GTT GAC
Pro Tyr Glu Cys Gly Ile Gln Asn Glu Leu Ser Val Asp
```

FIG. 5c

```
            1220            1230            1240
             *               *               *
CAC AGC GAC CCA GTC ATC CTG AAT GTC CTC TAT GGC CCA
His Ser Asp Pro Val Ile Leu Asn Val Leu Tyr Gly Pro 1250            1260            1270            1280
     *               *               *               *
 GAC GAC CCC ACC ATT TCC CCC TCA TAC ACC TAT TAC CGT
 Asp Asp Pro Thr Ile Ser Pro Ser Tyr Thr Tyr Tyr Arg 1290            1300            1310            1320
     *               *               *               *
CCA GGG GTG AAC CTC AGC CTC TCC TGC CAT GCA GCC TCT
Pro Gly Val Asn Leu Ser Leu Ser Cys His Ala Ala Ser 1330            1340            1350            1360
     *               *               *               *
AAC CCA CCT GCA CAG TAT TCT TGG CTG ATT GAT GGG AAC
Asn Pro Pro Ala Gln Tyr Ser Trp Leu Ile Asp Gly Asn 1370            1380            1390            1400
         *               *               *               *
ATC CAG CAA CAC ACA CAA GAG CTC TTT ATC TCC ACC ATC
Ile Gln Gln His Thr Gln Glu Leu Phe Ile Ser Asn Ile 1410            1420            1430            1440
         *               *               *               *
ACT GAG AAG AAC AGC GGA CTC TAT ACC TGC CAG GCC AAT
Thr Glu Lys Asn Ser Gly Leu Tyr Thr Cys Gln Ala Asn 1450            1460            1470            1480
         *               *               *               *
AAC TCA GCC AGT GGC CAC AGC AGG ACT ACA GTC AAG ACA
Asn Ser Ala Ser Gly His Ser Arg Thr Thr Val Lys Thr 1490            1500            1510            1520
             *               *               *               *
ATC ACA GTC TCT GCG GAC GTG CCC AAG CCC TCC ATC TCC
Ile Thr Val Ser Ala Asp Val Pro Lys Pro Ser Ile Ser 1530            1540            1550            1560
         *               *               *               *
AGC AAC AAC TCC AAA CCC GTG GAG GAC AAG GAT GCT GTG
Ser Asn Asn Ser Lys Pro Val Glu Asp Lys Asp Ala Val 1570            1580            1590            1600
             *               *               *               *
GCC TTC ACC TGT GAA CCT GAG GCT CAG AAC ACA ACC TAC
Ala Phe Thr Cys Glu Pro Glu Ala Gln Asn Thr Thr Tyr 1610            1620            1630
                 *               *               *
CTG TGG TGG GTA AAT GGT CAG AGC CTC CCA GTC AGT CCC
Leu Trp Trp Val Asn Gly Gln Ser Leu Pro Val Ser Pro
```

FIG. 5d

```
       1640            1650            1660            1670
         *               *               *               *
   AGG CTG CAG CTG TCC AAT GGC AAC AGG ACC CTC ACT CTA
   Arg Leu Gln Leu Ser Asn Gly Asn Arg Thr Leu Thr Leu 1680            1690            1700            1710
         *               *               *               *
   TTC AAT GTC ACA AGA AAT GAC GCA AGA GCC TAT GTA TGT
   Phe Asn Val Thr Arg Asn Asp Ala Arg Ala Tyr Val Cys 1720            1730            1740            1750
         *               *               *               *
   GGA ATC CAG AAC TCA GTG AGT GCA AAC CGT AGT GAC CCA
   Gly Ile Gln Asn Ser Val Ser Ala Asn Arg Ser Asp Pro 1760            1770            1780            1790
         *               *               *               *
   GTC ACC CTG GAT GTC CTC TAT GGG CCG GAT ACC CCC ATC
   Val Thr Leu Asp Val Leu Tyr Gly Pro Asp Thr Pro Ile 1800            1810            1820            1830
         *               *               *               *
   ATT TCC CCC CCA GAC TCG TCT TAC CTT TCT GGA GCG AAC
   Ile Ser Pro Pro Asp Ser Ser Tyr Leu Ser Gly Ala Asn 1840            1850            1860            1870
         *               *               *               *
   CTC AAC CTC TCC TGC CAC TCG GCC TCT AAT CCA TCC CCG
   Leu Asn Leu Ser Cys His Ser Ala Ser Asn Pro Ser Pro 1880            1890            1900            1910
         *               *               *               *
   CAG TAT TCT TGG CGT ATC AAT GGG ATA CCG CAG CAA CAC
   Gln Tyr Ser Trp Arg Ile Asn Gly Ile Pro Gln Gln His 1920            1930            1940            1950
         *               *               *               *
   ACA CAA GTT CTC TTT ATC GCC AAA ATC ACG CCA AAT AAT
   Thr Gln Val Leu Phe Ile Ala Lys Ile Thr Pro Asn Asn 1960            1970            1980            1990
         *               *               *               *
   AAC GGG ACC TAT GCC TGT TTT GTC TCT AAC TTG GCT ACT
   Asn Gly Thr Tyr Ala Cys Phe Val Ser Asn Leu Ala Thr 2000            2010            2020
              *               *               *
   GGC CGC AAT AAT TCC ATA GTC AAG AGC ATC ACA GTC TCT
   Gly Arg Asn Asn Ser Ile Val Lys Ser Ile Thr Val Ser
```

FIG. 5e

```
       2030              2040              2050              2060
        *                 *                 *                 *
 GCA TCT GGA ACT TCT CCT GGT CTC TCA GCT GGG GCC ACT
 Ala Ser Gly Thr Ser Pro Gly Leu Ser Ala Gly Ala Thr 2070              2080              2090              2100
        *                 *                 *                 *
 GTC GGC ATC ATG ATT GGA GTG CTG GTT GGG GTT GCT CTG
 Val Gly Ile Met Ile Gly Val Leu Val Gly Val Ala Leu 2110              2120              2130              2140
        *                 *                 *                 *
 ATA TAG CAG CCC TGG TGT AGT TTC TTC ATT TCA GGA AGA CTG
 Ile 2150              2160              2170              2180              2190
        *                 *                 *                 *                 *
 ACA GTT GTT TTG CTT CTT CCT TAA AGC ATT TGC AAC AGC TAC 2200              2210              2220              2230
                   *                 *                 *                 *
          AGT CTA AAA TTG CTT CTT TAC CAA GGA TAT TTA CAG AAA ATA 2240              2250              2260              2270
                   *                 *                 *                 *
          CTC TGA CCA GAG ATC GAG ACC ATC CTA GCC AAC ATC GTG AAA 2280              2290              2300              2310
                   *                 *                 *                 *
          CCC CAT CTC TAC TAA AAA TAC AAA AAT GAG CTG GGC TTG GTG 2320              2330              2340              2350
              *                 *                 *                 *
       GCG CGC ACC TGT AGT CCC AGT TAC TCG GGA GGC TGA GGC AGG 2360              2370              2380              2390              2400
        *                 *                 *                 *                 *
 AGA ATC GCT TGA ACC CGG GAG GTG GAG ATT GCA GTG AGC CCA 2410              2420              2430              2440
                   *                 *                 *                 *
          GAT CGC ACC ACT GCA CTC CAG TCT GGC AAC AGA GCA AGA CTC 2450              2460              2470              2480
                   *                 *                 *                 *
          CAT CTC AAA AAG AAA AGA AAA GAA GAC TCT GAC CTG TAC TCT 2490              2500              2510              2520
                   *                 *                 *                 *
          TGA ATA CAA GTT TCT GAT ACC ACT GCA CTG TCT GAG AAT TTC 2530              2540              2550              2560
              *                 *                 *                 *
       CAA AAC TTT AAT GAA CTA ACT GAC AGC TTC ATG AAA CTG TCC
```

FIG. 5f

```
     2570          2580          2590          2600          2610
       *             *             *             *             *
ACC AAG ATC AAG CAG AGA AAA TAA TTA ATT TCA TGG GGA CTA
              2620          2630          2640          2650
                *             *             *             *
AAT GAA CTA ATG AGG ATA ATA TTT TCA TAA TTT TTT ATT TGA
              2660          2670          2680          2690
                *             *             *             *
AAT TTT GCT GAT TCT TTA AAT GTC TTG TTT CCC AGA TTT CAG
              2700          2710          2720          2730
                *             *             *             *
GAA ACT TTT TTT CTT TTA AGC TAT CCA CTC TTA CAG CAA TTT
              2740          2750          2760          2770
                *             *             *             *
GAT AAA ATA TAC TTT TGT GAA CAA AAA TTG AGA CAT TTA CAT
     2780          2790          2800          2810          2820
       *             *             *             *             *
TTT ATC CCT ATG TGG TCG CTC CAG ACT TGG GAA ACT ATT CAT
              2830
                *
GAA TAT TTA TAT TGT ATG
```

FIG. 5g

CDNA CODING FOR CARCINOEMBRYONIC ANTIGEN (CEA)

CROSS-REFERENCES TO RELATED APPLICATIONS

This application is a continuation of application Ser. No. 07/231,741, filed Aug. 12, 1988, now abandoned, which is a continuation-in-part of application Ser. No. 07/060,031 filed Jun. 19, 1987, now abandoned, which is a continuation-in-part of application Ser. No. 07/016,683 filed Feb. 19, 1987, now abandoned, which is a continuation-in-part of application Ser. No. 06/896,361 filed Aug. 13, 1986, now abandoned.

BACKGROUND OF THE INVENTION

1. Field of the Invention

The present invention concerns a nucleic acid sequence which codes for a carcinoembryonic antigen peptide sequence.

2. Background Information

Carcinoembryonic antigen ("CEA") was first described by Gold and Freedman, *J. Exp. Med.*, 121, 439–462, (1965). CEA is characterized as a glycoprotein of approximately 200,000 molecular weight with 50–60% by weight of carbohydrate. CEA is present during normal human fetal development, but only in very low concentration in the normal adult intestinal tract. It is produced and secreted by a number of different tumors.

CEA is a clinically useful tumor marker for the management of colorectal cancer patients. CEA can be measured using sensitive immunoassay methods. When presurgical serum levels of CEA are elevated, a postsurgical drop in serum CEA to the normal range typically indicates successful resection of the tumor. Postsurgical CEA levels that do not return to normal often indicate incomplete resection of the tumor or the presence of additional tumor sites in the patient. After returning to normal levels, subsequent rapid rises in serum CEA levels usually indicate the presence of metastages. Slower postsurgical rises from the normal level are most often interpreted to indicate the presence of new primary tumors not previously detected. Post surgical management of colon cancer patients is thus facilitated by the measurement of CEA.

CEA is a member of an antigen family. Because of this, the immunoassay of CEA by presently available methods is complicated by the fact that CEA is but one of several potentially reactive antigens. There have been at least sixteen CEA-like antigens described in the literature. Since some of these appear to be the same antigen described by different investigators, the actual number of different antigens is somewhat less than this number. Nonetheless, there is a complex array of cross-reactive antigens which can potentially interfere with an immunoassay of the CEA released by tumors. It is known that serum levels of CEA-like antigens are elevated in many non-cancerous conditions such an inflammatory liver diseases and also in smokers. It is important that immunoassays used for the monitoring of cancer patient status not be interfered with by these other CEA-like antigens. Conversely, it is important to be able to distinguish the antigens by immunoassay because of the possibility that different tumor types may preferentially express different forms of CEA. If so, then the ability to reliably measure the different forms of CEA might provide the means of diagnose or more successfully treat different forms of cancer.

U.S. Pat. No. 3,663,684, entitled "Carcinoembryonic Antigen and Diagnostic Method Using Radioactive Iodine", concerns purification and radioiodination of CEA for use in a RIA.

U.S. Pat. No. 3,697,638 describes that CEA is a mixture of antigens (Components A and B in this case). U.S. Pat. No. 3,697,638 mentions methods for separating and radioiodinating each component and their use in specific RIA's.

U.S. Pat. No. 3,852,415, entitled "Compositions for Use in Radioimmunoassay, as Substitute for Blood Plasma Extract in Determination of Carcinoembryonic Antigen" relates to the use of a buffer containing EDTA and bovine serum albumin as a substitute for plasma as a diluent for CEA RIA's.

U.S. Pat. No. 3,867,363, entitled "Carcinoembryonic Antigens", is directed to the isolation of CEA components A and B, their labelling and use in a RIA.

U.S. Pat. No. 3,927,193, entitled "Localization of Tumors by Radiolabelled Antibodies", concerns the use of radiolabelled anti-CEA antibodies in whole body tumor imaging.

U.S. Pat. No. 3,956,258, entitled "Carcinoembryonic Antigens", relates to the isolation of CEA components A and B.

U.S. Pat. No. 4,086,217, entitled "Carcinoembryonic Antigens", is directed to the isolation of CEA components A and B.

U.S. Pat. No. 4,140,753, entitled "Diagnostic Method and Reagent", concerns the purification of a CEA isomer called CEA-S1 and its use in a RIA.

U.S. Pat. No. 4,145,336, entitled "Carcinoembryonic Antigen Isomer", relates to the antigen CEA-S1.

U.S. Pat. No. 4,180,499, entitled "Carcinoembryonic Antigens", describes a process for producing CEA component B.

U.S. Pat. No. 4,228,236, entitled "Process of Producing Carcinoembryonic Antigen", is directed to the use of the established cell lines LS-174T and LS-180 or clones or derivatives thereof for the production of CEA.

U.S. Pat. No. 4,272,504, entitled "Antibody Adsorbed Support Method for Carcinoembryonic Antigen Assay", concerns two concepts for the radioimmunoassay of CEA. First, U.S. Pat. No. 4,272,504 relates to a sample pretreatment in the form of heating to 65° to 85° C. at pH 5 to precipitate and eliminate extraneous protein. Second, it describes the use of a solid phase antibody (either on beads or tubes) as a means to capture analyte and radiolabelled CEA tracer.

U.S. Pat. No. 4,299,815, entitled "Carcinoembryonic Antigen Determination", concerns diluting a CEA sample with water and pretreating by heating to a temperature below which precipitation of protein will occur. The pretreated sample is then immunoassayed using RIA, EIA, FIA or chemiluminescent immunoassay.

U.S. Pat. No. 4,349,528, entitled "Monoclonal Hybridoma Antibody Specific for High Molecular Weight Carcinoembryonic Antigen", is directed to a monoclonal antibody reacting with 180 kD CEA, but not with other molecular weight forms.

U.S. Pat. No. 4,467,031, entitled "Enzyme-Immunoassay for Carcinoembryonic Antigen", relates to a sandwich enzyme immunoassay for CEA in which the first of two anti-CEA monoclonal antibodies is attached to a solid phase and the second monoclonal is conjugated with peroxidase.

U.S. Pat. No. 4,489,167, entitled "Methods and Compositions for Cancer Detection", describes that CEA shares an antigenic determinant with alpha-acid glycoprotein (AG), which is a normal component of human serum. The method described therein concerns a solid-phase sandwich enzyme immunoassay using as one antibody an antibody recognizing AG and another antibody recognizing CEA, but not AG.

U.S. Pat. No. 4,578,349, entitled "Immunoassay for Carcinoembryonic Antigen (CEA)", is directed to the use of high salt containing buffers as diluents in CEA immunoassays.

EP 113072-A, entitled "Assaying Blood Sample for Carcinoembryonic Antigen - After Removal of Interfering Materials by Incubation with Silica Gel", relates to the removal from a serum of a plasma sample of interfering substances by pretreatment with silica gel. The precleared sample is then subjected to an immunoassay.

EP 102008-A, entitled "Cancer Diagnostics Carcinoembryonic Antigen - Produced from Perchloric Acid Extracts Without Electrophoresis", relates to a procedure for the preparation of CEA from perchloric acid extracts, without the use of an electrophoresis step.

EP 92223-A, entitled "Determination of Carcinoembryonic Antigen in Cytosol or Tissue - For Therapy Control and Early Recognition of Regression", concerns an immunoassay of CEA, not in serum or plasma, but in the cytosol fraction of the tumor tissue itself.

EP 83103759.6, entitled "Cytosole-CEA-Measurement as Predictive Test in Carcinoma, Particularly Mammacarcinoma", is similar to EP 92223-A.

EP 83303759, entitled "Monoclonal Antibodies Specific to Carcinoembryonic Antigen", relates to the production of "CEA specific" monoclonal antibodies and their use in immunoassays.

WO 84/02983, entitled "Specific CEA-Family Antigens, Antibodies Specific Thereto and Their Methods of Use", is directed to the use of monoclonal antibodies to CEA-meconium (MA)-, and NCA-specific epitopes in immunoassays designed to selectively measure each of these individual components in a sample.

All of the heretofore CEA assays utilize either monoclonal or polyclonal antibodies which are generated by immunizing animals with the intact antigen of choice. None of them address the idea of making sequence specific antibodies for the detection of a unique primary sequence of the various antigens. They do not cover the use of any primary amino acid sequence for the production of antibodies to synthetic peptides or fragments of the natural product. They do not include the concept of using primary amino acid sequences to distinguish the CEA family members. None of them covers the use of DNA or RNA clones for isolating the genes with which to determine the primary sequence.

| DEFINITIONS | |
|---|---|
| Nucleic Acid Abbreviations as Appearing, for example, in FIG. 1 and in FIG. 5: | |
| A | adenine |
| G | guanine |
| C | cytosine |
| T | thymidine |
| U | uracil |
| Amino Acid Abbreviations as Appearing, for example, in FIG. 1 and in FIG. 5.: | |

| -continued | |
|---|---|
| DEFINITIONS | |
| Asp | aspartic acid |
| Asn | asparagine |
| Thr | threonine |
| Ser | serine |
| Glu | glutamic acid |
| Gln | glutamine |
| Pro | proline |
| Gly | glycine |
| Ala | alanine |
| Cys | cysteine |
| Val | valine |
| Met | methionine |
| Ile | isoleucine |
| Leu | leucine |
| Tyr | Tyrosine |
| Phe | phenylalanine |
| Trp | tryptophan |
| Lys | lysine |
| His | histidine |
| Arg | arginine |

Nucleotide—A monomeric unit of DNA or RNA containing a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C and uracil ("U").

DNA Sequence—A linear array of nucleotides connected one to the other by phosphodiester bonds between the 3' and 5' carbons of adjacent pentoses.

Functional equivalents—It is well known in the art that in a DNA sequence some nucleotides can be replaced without having an influence on the sequence of the expression product. With respect to the peptide this term means that one or more amino acids which have no function in a particular use can be deleted or replaced by another one.

Codon—A DNA sequence of three nucleotides (a triplet) which encodes through mRNA an amino acid, a translation start signal or a translation termination signal. For example, the nucleotide triplets TTA, TTG, CTT, CTC, CTA and CTG encode the amino acid leucine ("Leu"), TAG, TAA and TGA are translation stop signals and ATG is a translation start signal.

Reading Frame—The grouping of codons during translation of mRNA into amino acid sequences. During translation, the proper reading frame must be maintained. For example, the sequence GCTGGTTGTAAG may be translated in three reading frames or phases, each of which affords a different amino acid sequence

```
GCT GGT TGT AAG    —   Ala—Gly—Cys—Lys
G CTG GTT GTA AG   —   Leu—Val—Val
GC TGG TTG TAA G   —   Trp—Leu—(STOP).
```

Polypeptide—A linear array of amino acids connected one to the other by peptide bonds between the alpha-amino and carboxy groups of adjacent amino acids.

Genome—The entire DNA of a cell or a virus. It includes inter alia the structural genes coding for the polypeptides of the cell or virus, as well as its operator, promoter and ribosome binding and interaction sequences, including sequences such as the Shine-Dalgarno sequences.

Structural Gene—A DNA sequence which encodes through its template or messenger RNA ("mRNA") a sequence of amino acids characteristic of a specific polypeptide.

Transcription—The process of producing mRNA from a structural gene.

Translation—The process of producing a polypeptide from mRNA.

Expression—The process undergone by a structural gene to produce a polypeptide. It is a combination of transcription and translation.

Plasmid—A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance ($Tet^R$) transforms a cell previously sensitive to tetracycline into one which is resistant to it. A cell transformed by a plasmid is called a "transformant".

Phage or Bacteriophage—Bacterial virus, many of which consist of DNA sequences encapsilated in a protein envelope or coat ("capsid protein").

Cloning Vehicle—A plasmid, phage DNA or other DNA sequence which is capable of replicating in a host cell, which is characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contains a marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction.

Recombinant DNA Molecule or Hybrid DNA—A molecule consisting of segments of DNA from different genomes which have been joined end-to-end outside of living cells and have the capacity to infect some host cell and be maintained therein.

Expression Control Sequence—A sequence of nucleotides that controls and regulates expression of structural genes when operatively linked to those genes. They include the lac system, the trp system, major operator and promoter regions of phage λ, the control region of fd coat protein and other sequences known to control the expression of genes of prokaryotic or eukaryotic cells of their viruses.

Transformation/Transfection—DNA or RNA is introduced into cells to allow gene expression. "Infected" referred to herein concerns the introduction of RNA or DNA by a viral vector into the host. "Injected" referred to herein concerns the microinjection (use of a small syringe) of DNA into a cell.

CEA-(a), CEA-(b), CEA-(c), CEA-(d) mentioned hereinbelow are members of the CEA family which are described in the examples below.

SUMMARY OF THE INVENTION

The present invention concerns new nucleic acid sequences, e.g., DNA or RNA sequences, comprising a base sequence which codes for a CEA peptide sequence or nucleic acids having a base sequence (DNA or RNA) that is hybridizable therewith. Such nucleic acid can be a genomic DNA comprising a complete CEA gene or a portion thereof, including intron sequences, as well as exon sequences, or can be a DNA constructed to be complementary to messenger RNA coding for the CEA protein, i.e., cDNA. A nucleic acid sequence of the present invention comprises the DNA sequence set forth below or a fragment thereof, as well as sequences hybridizable therewith:

| 1 | GGGGTTTACA | CAACCACCAC | CCCATCAAAC | CCTTCATCAC | CAGCAACAAC | TCCAACCCCG |
|---|---|---|---|---|---|---|
| 61 | TGGAGGATGA | GGATGCTGTA | GCCTTAACCT | GTGAACCTGA | GATTCAGAAC | ACAACCTACC |
| 121 | TGTGGTGGGT | AAATAATCAG | AGCCTCGCGG | TCAGTCCCAG | GCTGCAGCTG | TCCAATGACA |
| 181 | ACAGGACCCT | CACTCTACTC | AGTGTCACAA | GCAATCATGT | ACGACCCTAT | GAGTGTGGAA |
| 241 | TCCAGAACGA | ATTAAGTGTT | GACCACAGCG | ACCCAGTCAT | CCTGAATGTC | CTCTATGGCC |
| 301 | CAGACGACCC | CACCATTTCC | CCCTCATACA | CCTATTACCG | TCCAGGGGTG | AACCTCAGCC |
| 361 | TCTCCTGCCA | TGCAGCCTCT | AACCCACCTG | CACAGTATTC | TTGGCTGATT | GATGGGAACA |
| 421 | TCCAGCAACA | CACACAAGAG | CTCTTTATCT | CCAACATCAC | TGAGAAGAAC | AGCGGACTCT |
| 481 | ATACCTGCCA | GGCCAATAAC | TCAGCCAGTG | GCCACAGCAG | GACTACAGTC | AAGACAATCA |
| 541 | CAGTGTGTGC | GGACGTGCCC | AAGCCCTCCA | TCTCCAGCAA | CAACTCCAAA | CCCGTGGAGG |
| 601 | ACAAGGATGC | TGTGGCCTTC | CACTGTGAAC | CTGAGGCTCA | GAACACAACC | TACCTGTGGT |
| 661 | GGGTAAATGG | TCAGAGCCTC | CCAGTCAGTC | CCAGGCTGCA | GCTGTCCAAT | GGCAACAGGA |
| 721 | CCCTCACTCT | ATTCAATGTC | ACAAGAAATG | ACGCAAGAGC | CTATGTATGT | GGAATCCAGA |
| 781 | ACTCAGTGAG | TGCAAACCGC | AGTGACCCAG | TCACCCTGGA | TGTCCTCTAT | GGGCCGGACA |
| 841 | CCCCCATCAT | TTCCCCCCCC | CC | | | |

Sequence displayed from position 1 to end (position 862)
Sequence numbered from position 1

The nucleic acid of the present invention which codes for the complete CEA protein and comprises the above sequence will have a total of no more than about 5000, more usually no more than about 3600, bases. Fragments of cDNA of the above sequences will have at least 10, and in some cases at least about 50, bases.

The above DNA sequence of 859 bases codes for an immunoreactive fragment of CEA which can be expressed, such as in lambda gt11. The sequence has an internal repeat sequence approximately 300 bases long and codes for a theoretical protein 285 amino acids long. This cDNA encodes for sequences found in other human genes and it is believed that this entire family of genes may code for the CEA family of proteins.

The present invention also concerns a DNA sequence having 2839 bp comprising the base sequence set forth below or a fragment thereof, as well as sequences hybridizable therewith;

```
           10          20          30          40          50
           •           •           •           •           •
  C ACC CTG GAG TCT CCC TCG GCC CCT CTC CAC AGA TGG TGC ATC CCC TGG CAG AGG CTC
```

```
        60              70              80              90             100             110
         •               •               •               •               •               •
CTG CTC ACA GCC TCA CTT CTA ACC TTC TGG AAC CCG CCC ACC ACT GCC AAG CTC ACT 120             130             140             150             160             170
             •               •               •               •               •               •
ATT GAA TCC ACG CCG TTC AAT GTC GCA GAG GGG AAG GAG GTG CTT CTA CTT GTC CAC 180             190             200             210             220
                 •               •               •               •               •
AAT CTG CCC CAG CAT CTT TTT GGC TAC AGC TGG TAC AAA GGT GAA AGA GTG GAT GGC 230             240             250             260             270             280
 •               •               •               •               •               •
AAC CGT CAA ATT ATA GGA TAT GTA ATA GGA ACT CAA CAA GCT ACC CCA GGG CCC GCA 290             300             310             320             330             340
         •               •               •               •               •               •
TAC AGT GGT CGA GAG ATA ATA TAC CCC AAT GCA TCC CTG CTG ATC CAG AAC ATC ATC 350             360             370             380             390             400
             •               •               •               •               •               •
CAG AAT GAC ACA GGA TTC TAC ACC CTA CAC GTC ATA AAG TCA GAT CTT GTG AAT GAA 410             420             430             440             450
                 •               •               •               •               •
GAA CCA ACT GGC CAG TTC CGG GTA TAC CCG GAG CTG CCC AAG CCC TCC ATC TCC AGC 460             470             480             490             500             510
 •               •               •               •               •               •
AAC AAC TCC AAA CCC GTG GAG GAC AAG GAT GCT GTG GCC TTC ACC TGT GAA CCT GAG 520             530             540             550             560             570
         •               •               •               •               •               •
ACT CAG GAC GCA ACC TAC CTG TGG TGG GTA AAC AAT CAG AGC CTC CCG GTC AGT CCC 580             590             600             610             620
             •               •               •               •               •
AGG CTG CAG CTG TCC AAT GGC AAC AGG ACC CTC ACT CTA TTC AAT GTC ACA AGA AAT 630             640             650             660             670             680
 •               •               •               •               •               •
GAA CAA GCA AGC TAC AAA TGT GAA ACC CAG AAC CCA GTG AGT GCC AGG CGC AGT GAT 690             700             710             720             730             740
         •               •               •               •               •               •
TCA GTC ATC CTG AAT GTC CTC TAT GGC CCG GAT GCC CCC ACC ATT TCC CCT CTA AAC 750             760             770             780             790
             •               •               •               •               •
ACA TCT TAC AGA TCA GGG GAA AAT CTG AAC CTC TCC TGC CAC GCA GCC TCT AAC CCA 800             810             820             830             840             850
 •               •               •               •               •               •
CCT GCA CAG TAC TCT TGG TTT GTC AAT GGG ACT TTC CAG CAA TCC ACC CAA GAG CTC 860             870             880             890             900             910
         •               •               •               •               •               •
TTT ATC CCC AAC ATC ACT GTG AAT AAT AGT GGA TCC TAT ACG TGC CAA GCC CAT AAC 920             930             940             950             960             970
             •               •               •               •               •               •
TCA GAC ACT GGC CTC AAT AGG ACC ACA GTC ACG ACG ATC ACA GTC TAT GCA GAG CCA 980             990            1000            1010            1020
```

-continued

CCC AAA CCC TTC ATC ACC AGC AAC AAC TCC AAC CCC GTG GAG GAT GAG GAT GCT GTA

```
      1030         1040         1050         1060         1070         1080
```
GCC TTA ACC TGT GAA CCT GAG ATT CAG AAC ACA ACC TAC CTG TGG TGG GTA AAT AAT

```
      1090         1100         1110         1120         1130         1140
```
CAG AGC CTC CCG GTC ATG CCC AGG CTG CAG CTG TCC AAT GAC AAC AGG ACC CTC ACT

```
      1150         1160         1170         1180         1190
```
CTA CTC AGT GTC ACA AGC AAT GAT GTA GGA CCC TAT GAG TGT GGA ATC CAG AAC GAA

```
      1200         1210         1220         1230         1240         1250
```
TTA AGT GTT GAC CAC AGC GAC CCA GTC ATC CTG AAT GTC CTC TAT GGC CCA GAC GAC

```
      1260         1270         1280         1290         1300         1310
```
CCC ACC ATT TCC CCC TCA TAC ACC TAT TAC CGT CCA GGG GTG AAC CTC AGC CTC TCC

```
      1320         1330         1340         1350         1360
```
TGC CAT GCA GCC TCT AAC CCA CCT GCA CAG TAT TCT TGG CTG ATT GAT GGG AAC ATC

```
1370         1380         1390         1400         1410         1420
```
CAG CAA CAC ACA CAA GAG CTC TTT ATC TCC AAC ATC ACT GAG AAG AAC AGC GGA CTC

```
      1430         1440         1450         1460         1470         1480
```
TAT ACC TGC CAG GCC AAT AAC TCA GCC AGT GGC CAC AGC AGG ACT ACA GTC AAG ACA

```
      1490         1500         1510         1520         1530         1540
```
ATC ACA GTC TCT GCG GAC GTG CCC AAG CCC TCC ATC TCC AGC AAC AAC TCC AAA CCC

```
      1550         1560         1570         1580         1590
```
GTG GAG GAC AAG GAT GCT GTG GCC TTC ACC TGT GAA CCT GAG GCT CAG AAC ACA ACC

```
      1600         1610         1620         1630         1640         1650
```
TAC CTG TGG TGG GTA AAT GGT CAG AGC CTC CCA GTC AGT CCC AGG CTG CAG CTG TCC

```
      1660         1670         1680         1690         1700         1710
```
AAT GGC AAC AGG ACC CTC ACT CTA TTC AAT GTC ACA AGA AAT GAC GCA AGA GCC TAT

```
      1720         1730         1740         1750         1760
```
GTA TGT GGA ATC CAG AAC TCA GTG AGT GCA AAC CGC AGT GAC CCA GTC ACC CTG GAT

```
      1770         1780         1790         1800         1810         1820
```
GTC CTC TAT GGG CCG GAC ACC CCC ATC ATT TCC CCC CCA GAC TCG TCT TAC CTT TCG

```
      1830         1840         1850         1860         1870         1880
```
GGA GCG AAC CTC AAC CTC TCC TGC CAC TCG GCC TCT AAC CCA TCC CCG CAG TAT TCT

```
      1890         1900         1910         1920         1930
```
TGG CGT ATC AAT GGG ATA CCG CAG CAA CAC ACA CAA GTT CTC TTT ATC GCC AAA ATC

-continued

```
1940            1950            1960            1970            1980           1990
  •               •               •               •               ••
ACG CCA AAT AAT AAC GGG ACC TAT GCC TGT TTT GTC TCT AAC TTG GCT ACT GGC CGC 2000            2010            2020            2030            2040            2050
        •               •               •               •               •               •
AAT AAT TCC ATA CTC AAG AGC ATC ACA GTC TCT GCA TCT GGA ACT TCT CCT GGT CTC 2060            2070            2080            2090            2100            2110
              •               •               •               •               •               •
TCA GCT GGG GCC ACT GTC GGC ATC ATG ATT GGA GTG CTG GTT GGG GTT GCT CTG ATA 2120            2130            2140            2150            2160
                    •               •               •               •               •
TAG CAG CCC TGG TGT AGT TTC TTC ATT TCA GGA AGA CTG ACA GTT GTT TTG CTT CTT 2170            2180            2190            2200            2210            2220
        •               •               •               •               •               •
CCT TAA AGC ATT TGC AAC AGC TAC AGT CTA AAA TTG CTT CTT TAC CAA GGA TAT TTA 2230            2240            2250            2260            2270            2280
              •               •               •               •               •               •
CAG AAA ATA CTC TGA CCA GAG ATC GAG ACC ATC CTA GCC AAC ATC GTG AAA CCC CAT 2290            2300            2310            2320            2330
                    •               •               •               •               •
CTC TAC TAA AAA TAC AAA AAT GAG CTG CGC TTG GTC GCG CGC ACC TGT AGT CCC AGT 2340            2350            2360            2370            2380            2390
        •               •               •               •               •               •
TAC TCG GGA GGC TGA GGC AGG AGA ATC GCT TGA ACC CGG GAG GTG GAG ATT GCT GTG 2400            2410            2420            2430            2440            2450
              •               •               •               •               •               •
AGC CCA GAT CGC ACC ACT GCA CTC CAG TCT GGC AAC AGA GCA AGA CTC CAT CTC AAA 2460            2470            2480            2490            2500
                    •               •               •               •               •
AAG AAA AGA AAA GAA GAC TCT GAC CTG TAC TCT TGA ATA CAA GTT TCT GAT ACC ACT 2510            2520            2530            2540            2550            2560
  •               •               •               •               •               •
GCA CTG TCT GAG AAT TTC CAA AAC TTT AAT GAA CTA ACT GAC AGC TTC ATC AAA CTG 2570            2580            2590            2600            2610            2620
        •               •               •               •               •               •
TCC ACC AAG ATC AAG CAG AGA AAA TAA TTA ATT TCA TGG GGA CTA AAT GAA CTA ATG 2630            2640            2650            2660            2670            2680
              •               •               •               •               •               •
AGG ATA ATA TTT TCA TAA TTT TTT ATT TGA AAT TTT GCA GAT TCT TTA AAT GTC TTG 2690            2700            2710            2720            2730
                    •               •               •               •               •
TTT CCC AGA TTT CAG GAA ACT TTT TTT CTT TTA AGC TAT CCA CTC TTA CAG CAA TTT 2740            2750            2760            2770            2780            2790
        •               •               •               •               •               •
GAT AAA ATA TAC TTT TGT GAA CAA AAA TTG AGA CAT TTA CAT TTT ATC CCT ATG TGG 2800            2810            2820            2830
              •               •               •               •
TCG CTC CAG ACT TGG GAA ACT ATT CAT GAA TAT TTA TAT TGT ATG
```

Further sequences are shown in the examples hereinbelow which code for proteins which are also members of the CEA family.

The present invention is also directed to a replicable recombinant cloning vehicle ("vector") having an insert comprising a nucleic acid, e.g., DNA, which comprises a base sequence which codes for a CEA peptide or a base sequence hybridizable therewith.

This invention also relates to a cell that is transformed/transfected, infected or injected with the above described replicable recombinant cloning vehicle or nucleic acid hybridizable with the aforementioned cDNA. Thus the invention also concerns the transfection of cells using free nucleic acid, without the use of a cloning vehicle.

Still further, the present invention concerns a polypeptide expressed by the above described transfected, infected or injected cell, which polypeptide exhibits immunological cross-reactivity with a CEA, as well as labelled forms of the polypeptide. The invention also relates to polypeptides having an amino acid sequence, i.e., synthetic peptides, of the expression product of a cell that is transfected, injected, infected with the above described replicable recombinant cloning vehicles, as well as labelled forms thereof. Stated otherwise, the present invention concerns a synthetic peptide having an amino acid sequence corresponding to the entire amino acid sequence or a portion thereof having no less than five amino acids of the aforesaid expression product.

The invention further relates to an antibody preparation specific for the above described polypeptide.

Another aspect of the invention concerns an immunoassay method for detecting CEA or a functional equivalent thereof in a test sample comprising
(a) contacting the sample with the above described antibody preparation, and
(b) determining binding thereof to CEA in the sample.

The invention also is directed to a nucleic acid hybridization method for detecting a CEA or a related nucleic acid (DNA or RNA) sample in a test sample comprising
(a) contacting the test sample with a nucleic acid probe comprising a nucleic acid, which comprises a base sequence which codes for a CEA peptide sequence or a base sequence that is hybridizable therewith, and
(b) determining the formation of the resultant hybridized probe.

The present invention also concerns a method for detecting the presence of carcinoembryonic antigen or a functional equivalent thereof in an animal or human patient in vivo comprising
a) introducing into said patient a labeled (e.g., a radioopaque material that can be detected by X-rays, radiolabeled or labeled with paramagnetic materials that can be detected by NMR) antibody preparation according to the present invention and
b) detecting the presence of such antibody preparation in the patient by detecting the label.

In another aspect, the present invention relates to the use of an antibody preparation according to the present invention for therapeutic purposes, namely, attaching to an antibody preparation radionuclides or toxins to form a complex and introducing an effective amount of such complex into an animal or human patient, e.g., by injection or orally. The labeled complex would attach to CEA in a patient and the radionuclide or toxin would serve to destroy the CEA expressing cell.

BRIEF DESCRIPTION OF THE DRAWINGS

FIGS. 1a and 1b together depict an amino acid and nucleic acid sequence (859 bases) of a cDNA sequence according to the present invention.

FIGS. 5a, 5b, 5c, 5d, 5e, 5f and 5g together depict amino acid and nucleic acid sequence (2839 bases) of a cDNA sequence according to the present invention. In FIG. 5a, the first amino acid for residue sequence purposes is Lys in the third row fourth amino acid from the right. Thereafter, the remaining amino acids are numbered consecutively.

DETAILED DESCRIPTION OF THE INVENTION

Figure 2:
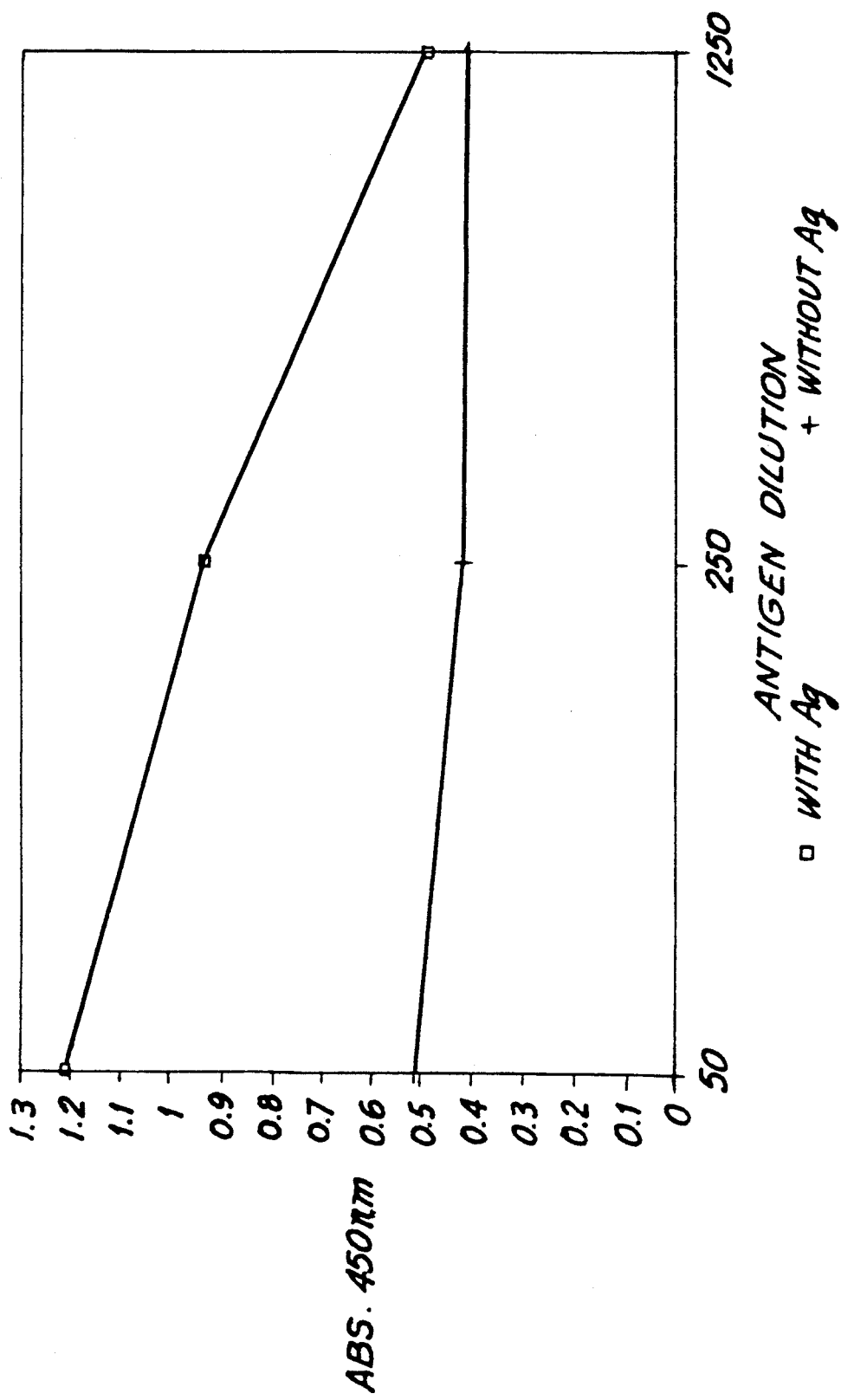
FIG. 2 is a graph depicting an enzyme immunoassay of CEA fusion protein according to the present invention with and without antigen ("Ag").

Some CEA epitopes are unique. These are the epitopes which have been useful for distinguishing the various CEA-like antigens immunologically. Peptide epitopes are defined by the linear amine acid sequence of the antigen and/or features resulting from protein folding. The information required for protein folding is encoded in the primary amino acid sequence. Therefore, antigenic differences ultimately result from differences in the primary structure of the different CEA molecules. The differences residing in the CEA protein in the CEA species can thus be determined by determining the primary amino acid sequences. This can be most readily accomplished by cloning and sequencing each of the genes for CEA. To determine which gene products will be most useful for cancer diagnosis, unique probes can be selected for each gene and expression of each gene can be determined in different tumor types by nucleic acid hybridization techniques. The present invention provides a tool with which to identify potential genes coding for different members of the CEA family and to determine the theoretical primary amino acid sequences for them. Using the method of automated peptide synthesis, peptides can then be synthesized corresponding to unique sequences in these antigens. With these peptides, antibodies to these sequences can be produced which, in the intact CEA molecule, might not be recognized by the animal being immunized. Having accomplished this, advantage can then be taken of the differences in these antigens to generate specific immunoassays for the measurement of each antigen.

A wide variety of host/cloning vehicle combinations may be employed in cloning the double-stranded nucleic acid prepared in accordance with this invention. For example, useful cloning vehicles may consist of segments of chromosomal, non-chromosomal and synthetic DNA sequences, such as various known derivatives of SV40 and known bacterial plasmids, e.g., plasmids from E. coli including col E1, pCR1, pBR322, pMB89 and their derivatives, wider host range plasmids, e.g., RP4, and phage DNAs, e.g., the numerous derivatives of phage, e.g., NM989, and other DNA phages, e.g., M13 and Filamenteous single-stranded DNA phages and vectors derived from combinations of plasmids and phage DNAs such as plasmids which have been modified to employ phage DNA or other expression control sequences or yeast plasmids such as the 2μplasmid or derivatives thereof. Useful hosts may include bacterial hosts such as strains of *E. coli*, such as *E. coli* HB 101, *E. coli* X1776, *E. coli* X2282, *E. coli* MRC1 and strains of Pseudomonas, *Bacillus subtilis, Bacillus stearothermophilus* and other *E. coli*, bacilli, yeasts and other fungi, animal or plant hosts such as animal (including human) or plant cells in culture or other hosts. Of course, not all host/vector combinations may be equally efficient. The particular selection of host/cloning vehicle combination may be made by those of skill in the art after due consideration of the principles set forth without departing from the scope of this invention.

Furthermore, within each specific cloning vehicle, various sites may be selected for insertion of the nucleic acid according to the present invention. These sites are usually designated by the restriction endonuclease which cuts them. For example, in pBR322 the Pst1 site is located in the gene for beta-lactamase, between the nucleotide triplets that code for amino acids 181 and 182 of that protein. One of the two HindII endonuclease recognition sites is between the triplets coding for amino acids 101 and 102 and one of the several Taq sites at the triplet coding for amino acid 45 of beta-lactamase in pBR322. In similar fashion, the EcoRI site and the PVUII site in this plasmid lie outside of any coding region, the EcoR1 site being located between the genes coding for resistance to tetracycline and ampicillin, respectively. These sites are well recognized by those of skill in the art. It is, of course, to be understood that a cloning vehicle useful in this invention need not have a restriction endonuclease site for insertion of the chosen DNA fragment. Instead, the vehicle could be cut and joined to the fragment by alternative means.

The vector or cloning vehicle and in particular the site chosen therein for attachment of a selected nucleic acid fragment to form a recombinant nucleic acid molecule is determined by a variety of factors, e.g., the number of sites susceptible to a particular restriction enzyme, the size of the protein to be expressed, the susceptibility of the desired protein to proteolytic degradation by host cell enzymes, the contamination of the protein to be expressed by host cell proteins difficult to remove during purification, the expression characteristics, such as the location of start and stop codons relative to the vector sequences, and other factors recognized by those of skill in the art. The choice of a vector and an insertion site for a particular gene is determined by a balance of these factors, not all sections being equally effective for a given case.

Methods of inserting nucleic acid sequences into cloning vehicles to form recombinant nucleic acid molecules include, for example, dA-dT tailing, direct ligation, synthetic linkers, exonuclease and polymerase-linked repair reactions followed by ligation, or extension of the nucleic acid strand with an appropriate polymerase and an appropriate single-stranded template followed by ligation.

It should also be understood that the nucleotide sequences or nucleic acid fragments inserted at the selected site of the cloning vehicle may include nucleotides which are not part of the actual structural gene for the desired polypeptide or mature protein or may include only a fragment of the complete structural gene for the desired protein or mature protein.

The cloning vehicle or vector containing the foreign gene is employed to transform an appropriate host so as to permit that host to replicate the foreign gene and to express the protein coded by the foreign gene or portion thereof. The selection of an appropriate host is also controlled by a number of factors recognized by the art. These include, for example, the compatibility with the chosen vector, the toxicity of proteins encoded by the hybrid plasmid, the ease of recovery of the desired protein, the expression characteristics, biosafety and costs. A balance of these factors must be struck with the understanding that not all hosts may be equally effective for expression of a particular recombinant DNA molecule.

The level of production of a protein is governed by two major factors: the number of copies of its gene within the cell and the efficiency with which those gene copies are transcribed and translated. Efficiency of transcription and translation (which together comprise expression) is in turn dependent upon nucleotide sequences, normally situated ahead of the desired coding sequence. These nucleotide sequences or expression control sequences define inter alia, the location at which RNA polymerase interacts to initiate transcription (the promoter sequence) and at which ribosomes bind and interact with the mRNA (the product of transcription) to initiate translation. Not all such expression control sequences function with equal efficiency. It is thus of advantage to separate the specific coding sequences for the desired protein from their adjacent nucleotide sequences and fuse them instead to other known expression control sequences so as to favor higher levels of expression. This having been achieved, the newly engineered nucleic acid, e.g., DNA, fragment may be inserted into a multicopy plasmid or a bacteriophage derivative in order to increase the number of gene copies within the cell and thereby further improve the yield of expressed protein.

Several expression control sequences may be employed as described above. These include the operator, promoter and ribosome binding and interaction sequences (including sequences such as the Shine-Dalgarno sequences) of the lactose operon of *E. coli* ("the lac system"), the corresponding sequences of the tryptophan synthetase system of *E. coli* ("the trp system"), the major operator and promoter regions of phage λ ($O_LP_L$ and $O_RP'_R$), the control region of Filamenteous single-stranded DNA phages, or other sequences which control the expression of genes of prokaryotic or eukaryotic cells and their viruses. Therefore, to improve the production of a particular polypeptide in an appropriate host, the gene coding for that polypeptide may be selected and removed from a recombinant nucleic acid molecule containing it and reinserted into a recombinant nucleic acid molecule closer or in a more appropriate relationship to its former expression control sequence or under the control of one of the above described expression control sequences. Such methods are known in the art.

As used herein "relationship" may encompass many factors, e.g., the distance separating the expression enhancing and promoting regions of the recombinant nucleic acid molecule and the inserted nucleic acid sequence, the transcription and translation characteristics of the inserted nucleic acid sequence or other sequences in the vector itself, the particular nucleotide sequence of the inserted nucleic acid sequence and other sequences of the vector and the particular characteristics of the expression enhancing and promoting regions of the vector.

Further increases in the cellular yield of the desired products depend upon an increase in the number of genes that can be utilized in the cell. This is achieved, for illustration purposes, by insertion of recombinant nucleic acid molecules engineered into the temperate bacteriophage λ (NM989), most simply by digestion of the plasmid with a restriction enzyme, to give a linear molecule which is then mixed with a restricted phage λ cloning vehicle (e.g., of the type described by N. E. Murray et al, "Lambdoid Phages That Simplify the Recovery of In Vitro Recombinants", *Molec. Gen. Genet.*, 150, pp. 53-61 (1977) and N. E. Murray et al, "Molecular Cloning of the DNA Ligase Gene From Bacteriophage T4", *J. Mol. Biol.*, 132, pp. 493-505 (1979)) and the recombinant DNA molecule recircularized by incubation with DNA ligase. The desired recombinant phage is then selected as before and used to lysogenize a host strain of *E. coli*.

Particularly useful λ cloning vehicles contain a temperature-sensitive mutation in the repression gene cl and suppressible mutations in gene S, the product of which is necessary for lysis of the host cell, and gene E, the product of which is major capsid protein of the virus. With this system, the lysogenic cells are grown at 32° C. and then heated to 45° C. to induce excision of the prophage. Prolonged growth at 37° C. leads to high levels of production of the protein, which is retained within the cells, since these are not lysed by phage gene products in the normal way, and since the phage gene insert is not encapsulated it remains available for further transcription. Artificial lysis of the cells then releases the desired product in high yield.

In addition, it should be understood that the yield of polypeptides prepared in accordance with this invention may also be improved by substituting different codons for some or all of the codons of the present DNA sequences, these substituted codons coding for amino acids identical to those coded for by the codons replaced.

Finally, the activity of the polypeptides produced by the recombinant nucleic acid molecules of this invention may be improved by fragmenting, modifying or derivatizing the nucleic acid sequences or polypeptides of this invention by well-known means, without departing from the scope of this invention.

The polypeptides of the present invention include the following:

(1) the polypeptides expressed by the above described cells,
(2) polypeptides prepared by synthetic means,
(3) fragments of polypeptides (1) or (2) above, such fragments produced by synthesis of amino acids or by digestion or cleavage.

Regarding the synthetic peptides according to the invention, chemical synthesis of peptides is described in the following publications: S. B. H. Kent, *Biomedical Polymers*, eds. Goldberg, E. P. and Nakajima, A. (Academic Press, New York), 213-242, (1980); A. R. Mitchell, S. B. H. Kent, M. Engelhard and R. B. Merrifield, *J. Org. Chem.*, 43, 2845-2852, (1978); J. P. Tam, T. -W. Wong, M. Riemen, F. -S. Tjoeng and R. B. Merrifield, *Tet. Letters*, 4033-4036, (1979); S. Mojsov, A. R. Mitchell and R. B. Merrifield, *J. Org. Chem.*, 45, 555-560, (1980); J. P. Tam, R. D. DiMarchi and R. B. Merrifield, *Tet. Letters*, 2851-2854, (1981); and S. B. H. Kent, M. Riemen, M. Le Doux and R. B. Merrifield. *Proceedings of the IV International Symposium on Methods of Protein Sequence Analysis*, (Brookhaven Press, Brookhaven, N.Y.), in press, 1981.

In the Merrifield solid phase procedure, the appropriate sequence of L-amino acids is built up from the carboxyl terminal amino acid to the amino terminal amino acid. Starting with the appropriate carboxyl terminal amino acid attached to a polystyrene (or other appropriate) resin via chemical linkage to a chloromethyl group, benzhydrylamine group, or other reactive group of the resin, amino acids are added one by one using the following procedure. The peptide-resin is:

(a) washed with methylene chloride;
(b) neutralized by making for 10 minutes at room temperature with 5% (v/v) diisopropylethylamine (or other hindered base) in methylene chloride;
(c) washed with methylene chloride;
(d) an amount of amino acid equal to six times the molar amount of the growing peptide chain is activated by combining it with one-half as many moles of a carbodiimide (e.g., dicyclohexylcarbodiimide, or diisopropylcarbodiimide) for ten minutes at 0° C., to form the symmetric anhydride of the amino acid. The amino acid used should be provided originally as the N-alpha-tert.-butyloxycarbonyl derivative, with side chains protected with benzyl esters (e.g., aspartic or glutamic acids), benzyl ethers (e.g., serine, threonine, cysteine or tyrosine), benzyloxycarbonyl groups (e.g., lysine) or other protecting groups commonly used in peptide synthesis;
(e) the activated amino acid is reacted with the peptide-resin for two hours at room temperature, resulting in addition of the new amino acid to the end of the growing peptide chain;
(f) the peptide-resin is washed with methylene chloride;
(g) the N-alpha-(tert.-butyloxycarbonyl) group is removed from the most recently added amino acid by reacting with 30 to 65%, preferably 50% (v/v) trifluoroacetic acid in methylene chloride for 10 to 30 minutes at room temperature;
(h) the peptide-resin is washed with methylene chloride;
(i) steps (a) through (h) are repeated until the required peptide sequence has been constructed.

The peptide is then removed from the resin and simultaneously the side-chain protecting groups are removed, by reaction with anhydrous hydrofluoric acid containing 10% v/v of anisole or other suitable (aromatic) scavenger. Subsequently, the peptide can be purified by gel filtration, ion exchange, high pressure liquid chromatography, or other suitable means.

In some cases, chemical synthesis can be carried out without the solid phase resin, in which case the synthetic reactions are performed entirely in solution. The reactions are similar and well known in the art, and the final product is essentially identical.

Digestion of the polypeptide can be accomplished by using proteolytic enzymes, especially those enzymes whose substrate specificity results in cleavage of the polypeptide at sites immediately adjacent to the desired sequence of amino acids.

Cleavage of the polypeptide can be accomplished by chemical means. Particular bonds between amino acids can be cleaved by reaction with specific reagents. Examples include the following: bonds involving methionine are cleaved by cyanogen bromide: asparaginyl-glycine bonds are cleaved by hydroxylamine.

The following is a non-limiting list of sequences believed to be important for the purpose of making synthetic peptides and antibodies to them. Each antigen is categorized into three levels: 1) large regions containing potentially useful sites within; 2) sub regions of 1 and; 3) individual sites considered to be the prime targets for use as synthetic peptide antigens.

| Antigen | Size Category (see above) | Amino Acid from Residue | | Amino Acid to Residue |
|---|---|---|---|---|
| CEA | 1 | 135 | – | 386 |
| (see FIG. 5) | 2 | 174 | – | 220 |
| | | 285 | – | 386 |
| | 3 | 174 | – | 200 |
| | | 208 | – | 216 |
| | | 285 | – | 290 |
| | | 292 | – | 308 |
| | | 312 | – | 321 |
| | | 360 | – | 372 |
| | | 380 | – | 386 |
| FL-5 | 1 | 135 | – | 386 |
| (the sequence | | 411 | – | 492 |
| for FL-5 is | 2 | 174 | – | 220 |
| given herein- | | 285 | – | 389 |
| below) | 3 | 174 | – | 200 |
| | | 208 | – | 222 |
| | | 285 | – | 292 |
| | | 295 | – | 311 |
| | | 315 | – | 328 |
| | | 331 | – | 345 |
| | | 348 | – | 360 |
| | | 363 | – | 377 |
| | | 383 | – | 390 |
| BT 20 | 1 | 135 | – | 285 |
| (the sequence | 2 | 168 | – | 220 |
| for BT 20 is | 3 | 168 | – | 196 |
| given herein- | | 210 | – | 220 |
| below) | | 264 | – | 283 |

The present invention has the following advantages:
(1) The nucleic acid coding for CEA according to the invention can be used as a probe to isolate the complete gene of which it is a part.
(2) It can be used as a probe to isolate other members of the CEA gene family.
(3) It can be used as an oligonucleotide probe to determine the expression of this gene in various tumor types.
(4) The nucleotide sequence can be used to predict the primary amino acid sequence of the protein for production of synthetic peptides and can be used to distinguish members of the CEA family.
(5) The synthetic peptides derived from the above sequences can be used to produce sequence-specific antibodies.
(6) Immunoassays for each member of the CEA family can be produced with these sequence-specific antibodies and synthetic peptides.
(7) These immunoassays can be used as diagnostics for different types of cancer if it is determined that different members of the CEA family are clinically useful markers for different types of cancer.

Polypeptides according to the present invention are labelled by conventional means using radioactive moieties, e.g., $^{125}$I, enzymes, dyes and fluorescent compounds, just to name a few.

Several possible configurations for immunoassays according to the present invention can be used. The readout systems capable of being employed in these assays are numerous and non-limiting examples of such systems include fluorescent and colorimetric enzyme systems, radioisotopic labelling and detection and chemiluminescent systems. Two examples of immunoassay methods are as follows:

(1) An enzyme linked immunoassay (ELISA) using an antibody preparation according to the present invention (including Fab or F(ab)' fragments derived therefrom) to a solid phase (such as a microtiter plate or latex beads) is attached a purified anti-CEA antibody of a specificity other than that which is conjugated to the enzyme. This solid phase antibody is contacted with the sample containing CEA. After washing, the solid phase antibody-CEA complex is contacted with the conjugated anti-peptide antibody (or conjugated fragment). After washing away unbound conjugate, color or fluorescence is developed by adding a chromogenic or fluorogenic substrate for the enzyme. The amount of color or fluorescence developed is proportional to the amount of CEA in the sample.

(2) A competitive fluorometric immunoassay using fluorescently labelled peptide or synthetic peptides of the sequence specified by cLV7. In this example, the purified peptide expressed by cells or synthetic peptides thereof are fluorescently labelled. To a solid phase is attached a purified anti-CEA antibody. This solid phase is then contacted with sample containing CEA to which has been added fluorescent peptide probe. After binding, excess probe is washed away the amount of bound probe is quantitated. The amount of bound fluorescent probe will be inversely proportional to the amount of CEA in the sample.

In the nucleic acid hybridization method according to the present invention, the nucleic acid probe is conjugated with a label, for example, an enzyme, a fluorophore, a radioisotope, a chemiluminescent compound, etc. In the most general case, the probe would be contacted with the sample and the presence of any hybridizable nucleic acid sequence would be detected by developing in the presence of a chromogenic enzyme substrate, detection of the fluorophore by epifluorescence, by autoradiography of the radioisotopically labelled probe or by chemiluminescence. The detection of hybridizable RNA sequences can be accomplished by (1) a dot blot methodology or (2) an in situ hybridization methodology. Methods for these last two techniques are described by D. Gillespie and J. Bresser, "mRNA Immobilization in NaI: Quick Blots", *biotechniques*, 194–192, November/December 1983 and J. Lawrence and R. Singer, "Intracellular Localization of Messenger RNAs for Cytoskeletal Proteins", *Cell*, 45, 407–415, May 9, 1986, respectively. The readout systems can be the same as described above, e.g., enzyme labelling, radiolabelling, etc.

As stated above, the invention also relates to the use in medicine of the aforementioned complex of the invention.

The present invention provides a pharmaceutical composition containing as an active ingredient the complex of the invention in admixture with a solid, liquid or liquefied gaseous diluent.

The invention further provides a pharmaceutical composition containing as an active ingredient a complex of the invention in the form of a sterile and/or physiologically isotonic aqueous solution.

The invention also provides a medicament in dosage unit form comprising the complex of the invention.

The invention also provides a medicament in the form of tablets (including lozenges and granules), dragees, capsules, caplets, pills, ampoules or suppositories comprising the complex of the invention.

"Medicament" as used herein means physically discrete coherent portions suitable for medical administration. "Medicament in dosage unit form" as used herein means physically discrete coherent units suitable for medical administration, each containing a daily dose or a multiple or a sum-multiple of a daily dose of the compound of the invention in association with a carrier and/or enclosed within an envelope.

The pharmaceutical compositions according to the invention may, for example, take the form of suspensions, solutions and emulsions of the active ingredient in aqueous or non-aqueous diluents, syrups, granulates or powders.

The diluents to be used in pharmaceutical compositions (e.g., granulates) adapted to be formed into tablets, dragees, capsules, caplets and pills include the following: (a) fillers and extenders, (b) binding agents, (c) moisturizing agents, (d) disintegrating agents, (e) agents for retarding dissolution, (f) resorption accelerators, (g) surface active agents, (h) adsorptive carriers, (i) lubricants.

The tablets, dragees, capsules, caplets and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time.

The active ingredient can also be made up in microencapsulated form together, with one or several of the above-mentioned diluents.

For parenteral administration, solutions and emulsions should be sterile and, if appropriate, blood-isotonic.

In addition to the complex of the invention, the pharmaceutical compositions and medicaments according to the invention can also contain other pharmaceutically active compounds.

The discrete coherent portions constituting the medicament according to the invention will generally be adapted by virtue of their shape or packaging for medical administration and may be, for example, any of the following: tablets (including lozenges and granulates), pills, dragees, capsules, caplets, suppositories and ampoules. Some of these forms may be made up for delayed release of the active ingredient. Some, such as capsules, may include a protective envelope which renders the portions of the medicament physically discrete and coherent.

The product of the above-mentioned pharmaceutical compositions and medicaments is carried out by any method known in the art, for example, by mixing the active ingredient(s) with the diluent(s) to form a pharmaceutical composition (e.g., a granulate) and then forming the composition into the medicament (e.g., tablets).

It is envisaged that the active complex will be administered perorally, parenterally (for example, intramuscularly, intraperitoneally, subcutaneously or intravenously), rectally or locally.

EXAMPLES

EXAMPLES 1 TO 8

Preparation of LV7 cDNA Which Codes for CEA-(a)

EXAMPLE 1

RNA Preparation

Tumor messenger RNA was prepared by the proteinase K-phenol extraction method of J. Favolaro, E. Treisman and R. Kamen, *Methods in Enzymology*, 65, 718, Academic Press, Inc., (1980), followed by oligo dT cellulose chromatography to yield poly A+ RNA (3'-polyadenylated eucaryotic RNA containing most mRNA sequences that can be translated into polypeptides). To obtain approximately 1.2 mg of poly A+ RNA, approximately $5 \times 10^9$ LoVo cells (ATCC CCL 229) were harvested from $100 \times 850$ cm$^3$ roller bottles after late logarithmic growth. Cells were lysed by homogenization in an ice-cold solution of 140 mM NaCl, 1.5 mM MgCl$_2$, 10 mM Tris-HCl, pH 8, 0.5% NP40, 4 mM dithiothreitol and 20 units of placental ribonucelase inhibitor/ml. Sodium deoxycholate was then added to 0.2%. Cytoplasm and nuclei were separated by centrifugation of the homogenate at $12,000 \times g$ for 20 minutes. The cytoplasmic fraction was mixed with an equal volume of 0.2M Tris-HCl, pH 7.8, 25 mM EDTA, 0.3M NaCl, 2% sodium dodecyl sulfate and 400 µg/ml of proteinase K, incubated for 1 hour at 37° C., then extracted once with an equal volume of phenol/-chloroform (1:1/v:v) solution. Nucleic acids were obtained by ethanol precipitation of the separated aqueous phase. Total RNA was enriched for poly A+ RNA by passage in 0.5M NaCl, 10 mM Tris-HCl, pH 7.8, 0.1% sarcosyl through an oligo dT(12–18) cellulose column. After washing, bound RNA was eluted in the same solution without sodium chloride.

EXAMPLE 2

Reverse Transcription of mRNA

Five micrograms of poly A+ LoVo RNA were primed for reverse transcription with oligo dT(12–18). Fifty microliter reactions were performed for 90 minutes at 42° C. with 75 units AMV reverse transcriptase (Life Sciences, Inc., St. Petersburg, Fla., U.S.A.). RNA was removed by alkaline hydrolysis, and single-stranded cDNA was made double-stranded and blunt-ended by incubation with the large fragment (Klenow) of DNA polymerase I and T$_4$ DNA polymerase, respectively.

EXAMPLE 3

Cloning of pLV7 (plasmid LV7)

Synthetic EcoRI DNA linkers (5'pGGAATTCC 3') were attached to the ends of cDNA prepared as described in Example 2 by blunt-end ligation with excess T$_4$ DNA ligase (20 Weiss units). Excess linkers were removed by gel permeation chromatography through "SEPHADEX" G-50 (medium), EcoRI sticky ends were generated by cleavage with EcoRI restriction enzyme and fractionation by agarose exclusion chromatography on A15m (BioRad, Laboratories, Richmond, Calif., U.S.A.). DNA fragments greater than 500 bp were selected after sizing on agarose gels and were precipitated with 95% ethanol. DNA was resuspended in a small volume of 10 mM Tris-HCl, pH 7.8, 1 mM EDTA and added to an equimolar amount of 5' phosphatased and EcoRI terminated arms of lambda gt11 (Promega Biotech, Madison, Wis., U.S.A.). This phage has the advantageous property that foreign DNAs inserted at the EcoRI site of lambda gt11 are translated as part of the beta-galactosidase fusion protein that can be screened for immunoreactivity with antibodies to CEA. DNAs were ligated for 24 hours at a concentration of 100 to 200 μg/ml in the presence of $T_4$ DNA ligase. Three microliters of ligated DNA were added to an in vitro lambda packaging mix (Stratagene, San Diego, Calif., U.S.A.) and packaged particles were assayed by infecting E. coli host Y1088 (ATCC 37195). Of four million phage, 1.2 million were determined by beta-galactosidase complementation to have cDNA inserts in them.

EXAMPLE 4

Screening of Fusion Polypeptides by Immunoblotting

Fifty thousand phage were plated on E. coli Y1090 (ATCC 37197) for screening on each of twenty 150 mm dishes containing LB-broth with 10 mM $MgSO_4$ and 100 μg/ml of ampicillin. In some cases, phage stocks were prepared by amplification and titering prior to screening. Phage were grown lytically for 4 hours at 42° C., then nitrocellulose circles impregnated with 10 mM IPTG (isopropyl thiogalactoside) were placed on the surface of the dishes and incubated an additional 2 hours at 37° C. During this period, fusion protein synthesis was induced and proteins which were absorbed to the nitrocellulose matrix were screened in a modified ELISA format. In applicants' library some LoVo fusion proteins may express a portion of a CEA or CEA-related epitope that can be recognized by appropriate antibodies. Applicants took advantage of commercially-available antisera directed against native CEA (180 kd) and of in-house prepared antisera against reduced and alkylated CEA to detect antigens on the filters. These rabbit polyclonal antisera were diluted in PBS/T (phosphate buffered saline (50 mM Na phosphate, pH 7.3, (50 mM NaCl) containing 0.05% "TWEEN-20" and 0.01% thimerosal) and incubated for two hours to allow recognition of proteins adhering to nitrocellulose circles. Excess antibody was removed and rabbit IgG molecules bound to fusion proteins were detected by mouse anti-rabbit IgG antibody conjugated with alkaline phosphatase. Color detection was in the presence of 5-bromo-4-chloro-3-indolyl phosphate and nitroblue tetrazolium. Darkly staining plaque images were marked and keyed with the master phage plate for retrieval of potential positive areas. The phage continuing to express anti-CEA reactive peptides after repeated dilution and screening by immunoblotting and amplification of the assay were used to prepare DNA.

EXAMPLE 5

DNA Manipulation

Phage DNA was prepared according to T. Maniatis, E. F. Fritsch and J. Sambrook, *Molecular Cloning, A Laboratory Manual*, Cold Spring Harbor, (1982). DNA segments were isolated from low melting agarose gels and inserted for subcloning in Bluescribe plasmid vectors (Stratagene, San Diego, Calif., U.S.A.). DNA sequencing was performed by the dideoxy termination method of F. Sanger, S. Nicklen and A. R. Coolson, *Proc. Natl. Acad. Sci. (U.S.A.)*, 74, 5463–5467, (1977).

EXAMPLE 6

Detection of CEA Reactivity in lambda cLV7 (cDNA LV7) by Enzyme Immunoassay

Lambda cLV7 were induced in E. coli Y 1089 for 20 minutes with isopropyl thiogalactoside and grown for 1 hour at 37° C. Cells were centrifuged for 5 minutes in a Beckman Microfuge at room temperature. The cells were resuspended in 1% of the original volume in 50 mM Tris HCl, pH 7.5, containing 10 μg/ml of leupeptin and pepstatin, 10 mM EDTA, 1 mM phenylmethyl sulfonylfluoride and 0.01% thimerosal. The cells were frozen at −80° C., thawed and sonicated for 6 minutes at 0° C. The sonicated suspension was centrifuged and the supernatant fluid was assayed for CEA immunoreactivity by enzyme linked immunoassay. A Linbro 96 well microtiter plate was coated with 400 ng of mouse monoclonal anti-beta galactosidase antibody overnite at 4° C. The unbound antibody was washed away and the plate was blocked with PBS/T (phosphate buffered saline (50 mM Na phosphate, pH 7.3, 150 mM NaCl) containing 0.05% "TWEEN-20" and 0.01% thimerosal) for 3 hours at room temperature. The supernatant from the sonicated cells was diluted as in PBS/T and 100 μl of the diluted antigen was added to the antibody-coated wells. After incubation for 2 hours at room temperature, unbound antigen was washed away and diluted rabbit anti-CEA antibody was added in 100 μl of PBS/T. The plate was then incubated for 2 hours at room temperature. After washing, each well received 100 μl of horseradish peroxidase-conjugated IgG from goat anti-rabbit IgG in PBS/T. After incubation for 2 hours at room temperature, the wells were washed and peroxidase substrate (3,3,5,5'-tetramethylbenzidine and hydrogen peroxide) was added for 5 minutes. The color development reaction was stopped by addition of 50 μl of 8M sulfuric acid. An absorbance of 450 nm was determined for each well. The open squares in FIG. 2 represent wells receiving fusion protein antigen as described above. The + data points represent control wells treated as above, but receiving 100 μl of PBS/T instead of diluted fusion protein antigen.

EXAMPLE 7

Immunochemical Identification of lambda LV7 Fusion Protein

Figure 3:
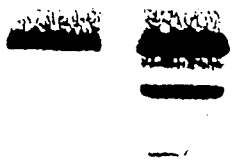
FIG. 3 is a pen and ink drawing that depicts an immunoblot of a CEA fusion protein according to the present invention.
Figure 4:
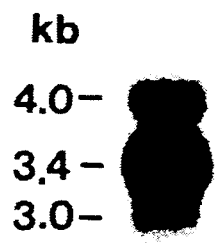
FIG. 4 is an autoradiograph of blots for the detection of a poly A+ RNA according to the present invention.

E. coli Y1089 lysate containing fusion protein was run on SDS-PAGE according to the method of U. K. Laemmli, *Nature (London)*, 227, 680–685 (1970). After electrophoresis on 10% acrylamide SDS-PAGE gels, proteins were electrophoretically transferred to nitrocellulose. After transfer, the filter was blocked in PBS/T. The immunoblot was developed by sequential incubation with rabbit anti-CEA and horseradish peroxidase-conjugated IgG from goat anti-rabbit IgG in PBS/T. After washing, the transfer was incubated with 4-chloro-1-naphthol to visualize the bands. Lane 1 in FIG. 3 is a control, namely, E. coli lysate without any phage. Lane 2 in FIG. 3 is a lysate containing lambda cLV7 fusion protein. The numbers on the left of FIG. 3 indicate the mobilities and molecular weights (in kilodaltons) of protein standards. The numbers on the right of FIG. 3 indicate the calculated molecular weight and mobility of lambda LV7 fusion protein (upper marker) and of E. coli beta-galactosidase subunit (lower marker).

EXAMPLE 8

Detection of cLV7-specific poly A+ RNA

Cytoplasmic poly A+ RNA was prepared from LoVo tumor cells and from the lymphoblastoid line GM1989 (control cell line). Five micrograms of each RNA was denatured and electrophoresed in a 1% agarose-2.2M formaldehyde gel and then transferred to nitrocellulose paper. Transfer blots were then challenged with $^{32}$P-radiolabelled cLV7 DNA in 2×SSPE, 5× Denhardt's, 50 μg/ml denatured salmon sperm DNA at 68° C. for 18 hours. Blots were washed in 0.2×SSPE, 0.25% SDS at 688° C. for 2 hours, then autoradiographed overnight on "KODAK" X-AR film with two intensifying screens. RNA size markers (BRL, Inc. Gaithersburg, Md., U.S.A.) were co-electrophoresed in adjacent wells of the agarose gel and visualized by staining with 0.04% methylene blue.

Results

Of nearly one million independently derived LoVo cDNA molecules inserted into the lambda gtll expression system and screened as polypeptides for anti-CEA immunoreactivity, two positive clones were isolated. Inserts were subcloned into the EcoRI site of Bluescribe (+) plasmid cloning vector and one of these, designated, pcLV7, was analyzed further. Deposited with the American Type Culture Collection ("ATCC") on Jul. 30, 1986 was a plasmid in *Escherichia Coli* containing pcLV7, ATCC No. 67169. By DNA sequence analysis, the insert size of this clone is 859 bp and its sequence is shown in FIG. 1. The upper line represents the nucleotide sequence of the open reading frame of pcLV7. Below it is the peptide sequence for which it codes. The general term used to designate the cDNA clone herein is cLV7 or LV7. When appended to this term, the prefixes lambda- or p- refer, respectively, to this clone as inserted into lambda phage or in plasmid.

EXAMPLES 9 to 13

Preparation of 1LV7 cDNA Which Codes for CEA-(b)

EXAMPLE 9

RNA Preparation

The same procedure of Example 1 for LV7 cDNA was followed for 1LV7 cDNA.

EXAMPLE 10

Reverse Transcription of mRNA

Fifty micrograms of poly A+ RNA were primed for reverse transcription with oligo dt$_{(12-18)}$ and random deoxyhexamers. The 350 microliter reaction was incubated for 2.5 hours at 42° C. with 900 units of AMV reverse transcriptase (Life Sciences Inc., St. Petersburg, Fla., U.S.A.). The RNA component of the cDNA/RNA hybrids was then replaced with the cDNA complementary strand by treatment with RNase H, *E. coli* DNA polymerase I and *E. coli* DNA ligase at 12° C. and 22° C. for 1.5 hours each. Molecular ends were polished by treatment with T$_4$ DNA polymerase.

EXAMPLE 11

Cloning of p1LV7

In order to protect EcoRI sites internal to the newly-synthesized cDNA from subsequent digestions steps, total cDNA was subjected to treatment with EcoRI methylase in the presence of 80 μM S-adenosyl methionine for 1 hour at 37° C. The DNA was then size-fractionated by electrophoresis through a 1% low melting point agarose gel. cDNA segments in the size range of 2 to 5 kb were excised, extracted from the gel slice and incubated in the presence of a 100-fold molar excess of synthetic EcoRI linkers (5' pdGGAATTCC 3') with T$_4$ DNA ligase. Excess linkers were removed by gel permeation chromatography through Sephadex G-50 (medium) and EcoRI sticky ends were generated by cleavage with EcoRI restriction enzyme. EcoRI terminated cDNA segments were incubated with EcoRI cleaved and phosphatase arms of bacteriophage vector lambda gtll in the presence of T$_4$ DNA ligase at 5° C. overnight. Aliquots of the ligation mixture were then mixed with in vitro packaging extracts (Stratagene, San Diego, Calif., U.S.A.) and phage particles were titrated on *E. coli* Y1090 cells.

EXAMPLE 12

Screening of Recombinants by Hybridization

Fifty thousand phage (pfu) from the in vitro packaged library were plated on each of four 150 mm LB plates containing 1.4% agar, 10 mM MgSO$_4$ and 100 μg/ml ampicillin. Phage were permitted to lyse host cells until plaque sizes were 0.2 to 0.5 mm in diameter. Plates were then cooled and nitrocellulose filter replicas were prepared by the method of W. D. Benton and R. W. Davis, "Screening Lambda GT Recombinant Clones by Hybridization to Single Plaques In Situ", *Science*, 196, 180–182, (1977). Filters were prehybridized and hybridized in 2×SSPE, 5× Denhardt's, 0.1% SDS, 100 ug/ml of denatured salmon sperm DNA and for the hybridization step, 2 ng/ml of $^{32}$P-labelled cLV7 insert DNA. Non-specific DNA hybridization was removed by washing filters in 0.5×SSPE, 0.25% SDS. Positive plaques were detected by autoradiography, picked and screened for two additional rounds of positive hybridization with radiolabeled probe.

EXAMPLE 13

DNA Manipulation

Inserts from the positive plaques from Example 12 were introduced into a bacterial plasmid vector, and exonuclease III-generated double stranded segments were sequenced by the dideoxy chain termination method. DNA sequences were computer-analyzed using Pustell DNA sequence analysis programs (IBI International, New Haven, Conn., U.S.A.).

Results

Of nearly two hundred thousand independently derived LoVo cDNA molecules inserted into lambda gt11 vector and screened for reactivity with a radiolabeled LV7 probe, forty positive phage were selected. The largest of these (approximately 3 Kb) was sequenced and its nucleic acid and protein sequence is given in FIG. 5.

Deposited with the ATCC on Feb. 6, 1987 was a plasmid in *Escherichia Coli* containing Pc1LV7, ATCC No. 67312.

By DNA sequence analysis, the insert size of this clone is 2839 bp and its sequence is shown in FIG. 5. The upper line represents the nucleotide sequence of the open reading frame of pc1LV7. Below it is the peptide sequence for which it codes. The general term used to designate the cDNA clone herein is c1LV7 or 1LV7. When appended to this term, the prefixes lambda- or p-refer, respectively, to this clone as inserted into lambda phage or in plasmid.

EXAMPLE 14

Cloning and Sequencing of cFL-CEA Which Codes for CEA-(c)

A recombinant library containing $2 \times 10^5$ independent inserts of fetal liver cDNA in bacteriophage vector lambda gt11 (Clontech, Palo Alto, Calif., U.S.A.) was screened with radiolabeled LV7 cDNA according to W. D. Benton and R. W. Davis, *Science*, 196, 180–182, (1977). A single positive clone was selected and the EcoRI insert was subcloned into plasmid vector Bluescript KS+ (Stratagene, San Diego, Calif., U.S.A.). The deletion clones were prepared in both directions and sequenced by the dideoxy chain termination method of F. Sanger, S. Nicklen and A. R. Coulson, *Proc. Natl. Acad. Sci., U.S.A.*, 74, 5463–5647, (1977). This clone, named FL5, was incomplete as judged by the lack of a translation termination signal. A single copy probe derived from the 3' end of FL5 was used to rescreen the commercial fetal liver library described above. Five positive clones were obtained, inserts were cloned into Bluescript KS+ vector, and the longest, named FL4, was sequenced. These two cDNA plasmids, FL5 and FL4 overlap and together contain the entire open reading frame of the polypeptide, designated herein as FL-CEA. The translated sequence of FL-CEA (ATCC No. 67711, deposited May 25, 1988) is as follows (a cDNA cloned from a cell transfectant and consisting of the full length FL-CEA sequence was deposited with the ATCC on May 25, 1988 and given the identification number 67710):

```
          10                          30                          50
CAGCCGTGCTCGAAGCGTTCCTGGAGCCCAAGCTCTCCTCCACAGGTGAAGACAGGGCCA 70                          90                         110
GCAGGAGACACCATGGGGCACCTCTCAGCCCCACTTCACAGAGTCCGTGTACCCTGGCAG
              Met Gly His Leu Ser Ala Pro Leu His Arg Val Arg Val Pro Trp Gln 130                         150                         170
GGGCTTCTGCTCACAGCCTCACTTCTAACCTTCTGGAACCCGCCCACCACTGCCCAGCTC
Gly Leu Leu Leu Thr Ala Ser Leu Leu Thr Phe Trp Asn Pro Pro Thr Thr Ala Gln Leu 190                         210                         230
ACTACTGAATCCATGCCATTCAATGTTGCAGAGGGGAAGGAGGTTCTTCTCCTTGTCCAC
Thr Thr Glu Ser Met Pro Phe Asn Val Ala Glu Gly Lys Glu Val Leu Leu Leu Val His 250                         270                         290
AATCTGCCCCAGCAACTTTTTGGCTACAGCTGGTACAAAGGGGAAAGAGTGGATGGCAAC
Asn Leu Pro Gln Gln Leu Phe Gly Tyr Ser Trp Tyr Lys Gly Glu Arg Val Asp Gly Asn 310                         330                         350
CGTCAAATTGTAGGATATGCAATAGGAACTCAACAAGCTACCCCAGGGCCCGCAAACAGC
Arg Gln Ile Val Gly Tyr Ala Ile Gly Thr Gln Gln Ala Thr Pro Gly Pro Ala Asn Ser 370                         390                         410
GGTCGAGAGACAATATACCCCAATGCATCCCTGCTGATCCAGAACGTCACCCAGAATGAC
Gly Arg Glu Thr Ile Tyr Pro Asn Ala Ser Leu Leu Ile Gln Asn Val Thr Gln Asn Asp 430                         450                         470
ACAGGATTCTACACCCTACAAGTCATAAAGTCAGATCTTGTGAATGAAGAAGCAACTGGA
Thr Gly Phe Tyr Thr Leu Gln Val Ile Lys Ser Asp Leu Val Asn Glu Glu Ala Thr Gly 490                         510                         530
CAGTTCCATGTATACCCGGAGCTGCCCAAGCCCTCCATCTCCAGCAACAACTCCACCCCT
Gln Phe His Val Tyr Pro Glu Leu Pro Lys Pro Ser Ile Ser Ser Asn Asn Ser Asn Pro 550                         570                         590
GTGGAGGACAAGGATGCTGTGGCCTTCACCTGTGAACCTGAGACTCAGGACACAACCTAC
Val Glu Asp Lys Asp Ala Val Ala Phe Thr Cys Glu Pro Glu Thr Gln Asp Thr Thr Tyr 610                         630                         650
CTGTGGTGGATAAACAATCAGAGCCTCCCGGTCAGTCCCAGGCTGCAGCTGTCCAATGGC
Leu Trp Trp Ile Asn Asn Gln Ser Leu Pro Val Ser Pro Arg Leu Gln Leu Ser Asn Gly 670                         690                         710
AACAGGACCCTCACTCTACTCAGTGTCACAAGGAATGACACAGGACCCTATGAGTGTGAA
Asn Arg Thr Leu Thr Leu Leu Ser Val Thr Arg Asn Asp Thr Gly Pro Tyr Glu Cys Glu
```

-continued

```
          730                              750                               770
ATACAGAACCCAGTGAGTGCGAACCGCAGTGACCCAGTCACCTTGAATGTCACCTATGGC
Ile  Gln  Asn  Pro  Val  Ser  Ala  Asn  Arg  Ser  Asp  Pro  Val  Thr  Leu  Asn  Val  Thr  Tyr  Gly 790                              810                               830
CCGGACACCCCCACCATTTCCCCTTCAGACACCTATTACCGTCCAGGGGCAAACCTCAGC
Pro  Asp  Thr  Pro  Thr  Ile  Ser  Pro  Ser  Asp  Thr  Tyr  Tyr  Arg  Pro  Gly  Ala  Asn  Leu  Ser 850                              870                               890
CTCTCCTGCTATGCAGCCTCTAACCCACCTGCACAGTACTCCTGGCTTATCAATGGAACA
Leu  Ser  Cys  Tyr  Ala  Ala  Ser  Asn  Pro  Pro  Ala  Gln  Tyr  Ser  Trp  Leu  Ile  Asn  Gly  Thr 910                              930                               950
TTCCAGCAAAGCACACAAGAGCTCTTTATCCCTAACATCACTGTGAATAATAGTGGATCC
Phe  Gln  Gln  Ser  Thr  Gln  Glu  Leu  Phe  Ile  Pro  Asn  Ile  Thr  Val  Asn  Asn  Ser  Gly  Ser 970                              990                              1010
TATACCTGCCACGCCAATAACTCAGTCACTGGCTGCAACAGGACCACAGTCAAGACGATC
Tyr  Thr  Cys  His  Ala  Asn  Asn  Ser  Val  Thr  Gly  Cys  Asn  Arg  Thr  Thr  Val  Lys  Thr  Ile 1030                             1050                              1070
ATAGTCACTGAGCTAAGTCCAGTAGTAGCAAAGCCCCAAATCAAAGCCAGCAAGACCACA
Ile  Val  Thr  Glu  Leu  Ser  Pro  Val  Val  Ala  Lys  Pro  Gln  Ile  Lys  Ala  Ser  Lys  Thr  Thr 1090                             1110                              1130
GTCACAGGAGATAAGGACTCTGTGAACCTGACCTGCTCCACAAATGACACTGGAATCTCC
Val  Thr  Gly  Asp  Lys  Asp  Ser  Val  Asn  Leu  Thr  Cys  Ser  Thr  Asn  Asp  Thr  Gly  Ile  Ser 1150                             1170                              1190
ATCCGTTGGTTCTTCAAAAACCAGAGTCTCCCGTCCTCGGAGAGGATGAAGCTGTCCCAG
Ile  Arg  Trp  Phe  Phe  Lys  Asn  Gln  Ser  Leu  Pro  Ser  Ser  Glu  Arg  Met  Lys  Leu  Ser  Gln 1210                             1230                              1250
GGCAACACCACCCTCAGCATAAACCCTGTCAAGAGGGAGGATGCTGGGACGTATTGGTGT
Gly  Asn  Thr  Thr  Leu  Ser  Ile  Asn  Pro  Val  Lys  Arg  Glu  Asp  Ala  Gly  Thr  Tyr  Trp  Cys 1270                             1290                              1310
GAGGTCTTCAACCCAATCAGTAAGAACCAAAGCGACCCCATCATGCTGAACGTAAACTAT
Glu  Val  Phe  Asn  Pro  Ile  Ser  Lys  Asn  Gln  Ser  Asp  Pro  Ile  Met  Leu  Asn  Val  Asn  Tyr 1330                             1350                              1370
AATGCTCTACCACAAGAAAATGGCCTCTCACCTGGGGCCATTGCTGGCATTGTGATTGGA
Asn  Ala  Leu  Pro  Gln  Glu  Asn  Gly  Leu  Ser  Pro  Gly  Ala  Ile  Ala  Gly  Ile  Val  Ile  Gly 1390                             1410                              1430
GTAGTGGCCCTGGTTGCTCTGATAGCAGTAGCCCTGGCATGTTTTCTGCATTTCGGGAAG
Val  Val  Ala  Leu  Val  Ala  Leu  Ile  Ala  Val  Ala  Leu  Ala  Cys  Phe  Leu  His  Phe  Gly  Lys 1450                             1470                              1490
ACCGGCAGGGCAAGCGACCAGCGTGATCTCACAGAGCACAAACCCTCAGTCTCCAACCAC
Thr  Gly  Arg  Ala  Ser  Asp  Gln  Arg  Asp  Leu  Thr  Glu  His  Lys  Pro  Ser  Val  Ser  Asn  His 1510                             1530                              1550
ACTCAGGACCACTCCAATGACCCACCTAACAAGATGAATGAAGTTACTTATTCTACCCTG
Thr  Gln  Asp  His  Ser  Asn  Asp  Pro  Pro  Asn  Lys  Met  Asn  Glu  Val  Thr  Tyr  Ser  Thr  Leu 1570                             1590                              1610
AACTTTGAAGCCCAGCAACCCACACAACCAACTTCAGCCTCCCCATCCCTAACAGCCACA
Asn  Phe  Glu  Ala  Gln  Gln  Pro  Thr  Gln  Pro  Thr  Ser  Ala  Ser  Pro  Ser  Leu  Thr  Ala  Thr 1630                             1650                              1670
GAAATAATTTATTCAGAAGTAAAAAAGCAGTAATGAAACCTGTCCTGCTCACTGCAGTGC
Glu  Ile  Ile  Tyr  Ser  Glu  Val  Lys  Lys  Gln 1690                             1710                              1730
TGATGTATTTCAAGTCTCTCACCCTCATCACTAGGAGATTCCTTTCCCCTGTAGGGTAGA
```

-continued

```
           1750                    1770                    1790
GGGGTGGGGACAGAAACAACTTTCTCCTACTCTTCCTTCCTAATAGGCATCTCCAGGCTG
           1810                    1830                    1850
CCTGGTCACTGCCCCTCTCTCAGTGTCAATAGATGAAAGTACATTGGGAGTCTGTAGGAA
           1870                    1890                    1910
ACCCAACCTTCTTGTCATTGAAATTTGGCAAAGCTGACTTTGGGAAAGAGGGACCAGAAC
           1930                    1950                    1970
TTCCCCTCCCTTCCCCTTTTCCCAACCTGGACTTGTTTTAAACTTGCCTGTTCAGAGCAC
           1990                    2010                    2030
TCATTCCTTCCCACCCCCAGTCCTGTCCTATCACTCTAATTCGGATTTGCCATAGCCTTG
           2050                    2070                    2090
AGGTAATGTCCTTTTCCATTAAGTACATGTGCCAGGAAACAGCGAGAGAGAGAAAGTAAA
           2110                    2130                    2150
CGGCAGTAATGCTTCTCCTATTTCTCCAAAGCCTTGTGTGAACTAGCAAAGAGAAGAAAA
           2170                    2190                    2210
TCAAATATATAACCAATAGTGAAATGCCACAGGTTTGTCCACTGTCAGGGTTGTCTACCT
           2230                    2250                    2270
GTAGGATCAGGGTCTAAGCACCTTGGTGCTTAGCTAGAATACCACCTAATCCTTCTGGCA
           2290                    2310                    2330
AGCCTGTCTTCAGAGAACCCACTAGAAGCAACTAGGAAAAATCACTTGCCAAAATCCAAG
           2350                    2370                    2390
GCAATTCCTGATGGAAAATGCAAAAGCACATATATGTTTTAATATCTTTATGGGCTCTGT
           2410                    2430                    2450
TCAAGGCAGTGCTGAGAGGGAGGGGTTATAGCTTCAGGAGGGAACCAGCTTCTGATAAAC
           2470                    2490                    2510
ACAATCTGCTAGGAACTTGGGAAAGGAATCAGAGAGCTGCCCTTCAGCGATTATTTAAAT
           2530                    2550                    2570
TGTTAAAGAATACACAATTTGGGGTATTGGGATTTTTCTCCTTTTCTCTGAGACATTCCA
           2590                    2610                    2630
CCATTTTAATTTTTGTAACTGCTTATTTATGTGAAAAGGGTTATTTTTACTTAGCTTAGC
           2650                    2670                    2690
TATGTCAGCCAATCCGATTGCCTTAGGTGAAAGAAACCACCGAAATCCCTCAGGTCCCTT
           2710                    2730                    2750
GGTCAGGAGCCTCTCAAGATTTTTTTTGTCAGAGGCTCCAAATAGAAAATAAGAAAAGGT
           2770                    2790                    2810
TTTCTTCATTCATGGCTAGAGCTAGATTTAACTCAGTTTCTAGGCACCTCAGACCAATCA
           2830                    2850                    2870
TCAACTACCATTCTATTCCATGTTTGCACCTGTGCATTTTCTGTTTGCCCCCATTCACTT
           2890                    2910                    2930
TGTCAGGAAACCTTGGCCTCTGCTAAGGTGTATTTGGTCCTTGAGAAGTGGGAGCACCCT
```

```
                                    -continued
2950                         2970                         2990

ACAGGGACACTATCACTCATGCTGGTGGCATTGTTTACAGCTAGAAAGCTGCACTGGTGC 3010                         3030                         3050

TAATGCCCCTTGGGAAATGGGGCTGTGAGGAGGAGGATTATAACTTAGGCCTAGCCTCTT 3070                         3090                         3110

TTAACAGCCTCTGAAATTTATCTTTTCTTCTATGGGGTCTATAAATGTATCTTATAATAA 3130                         3150                         3170

AAAGGAAGGACAGGAGGAAGACAGGCAAATGTACTTCTCACCCAGTCTTCTACACAGATG 3190                         3210                         3230

GAATCTCTTTGGGGCTAAGAGAAAGGTTTTATTCTATATTGCTTACCTGATCTCATGTTA 3250                         3270                         3290

GGCCTAAGAGGCTTTCTCCAGGAGGATTAGCTTGGAGTTCTCTATACTCAGGTACCTCTT 3310                         3330                         3350

TCAGGGTTTTCTAACCCTGACACGGACTGTGCATACTTTCCCTCATCCATGCTGTGCTGT 3370                         3390                         3410

GTTATTTAATTTTTCCTGGCTAAGATCATGTCTGAATTATGTATGAAAATTATTCTATGT 3430                         3450

TTTTATAATAAAAATAATATATCAGACATCGAAAAAAAAAA
```

For residue sequence purposes, the first amino acid is Gln which is under nucleic acid 190. Thereafter the amino acids are numbered consecutively.

EXAMPLES 15 TO 19

Cloning and Sequencing of cBT-20 Which Codes for CEA-(d)

EXAMPLE 15

RNA Preparation

Tumor messenger RNA was prepared by the proteinase K-phenol extraction method of Favolaro, Treisman and Kamen, *Methods in Enzymology*, 65, 718, (1980), followed by oligo dT-cellulose chromatography to yield poly A+ RNA. To obtain approximately 100 micrograms of pA+ RNA, 1 gram (wet weight) of BT-20 cells (ATCC HTB 19) were resuspended and lysed in 20 ml ice-cold RNA lysis buffer (140 mM NaCl, 1.5 mM MgCl$_2$, 10 mM Tris-HCl, pH 7.8, 0.5% NP-40 4 mM 2-mercatoethanol and 20 units of placental ribonuclease inhibitor per ml). Sodium desoxycholate was added to 0.2%. Cytoplasm and nuclei were separated by centrifugation of the homogenate at 12,000×g for 20 minutes. The cytoplasmic fraction was mixed with an equal volume of PK buffer (0.2M Tris-HCl, pH 7.8, 25 mM EDTA, 0.3M NaCl, 2% sodium dodecyl sulfate and 400 µg of proteinase K per ml), incubated for 2 hours at 37° C., then extracted once with an equal volume of phenol/chloroform (1:1/v:v) solution. Nucleic acids were obtained by ethanol precipitation of the separated aqueous phase. Total RNA was enriched for poly A+ RNA by passage in 0.5M NaCl, 10 mM Tris-HCl, pH 7.8, 0.1% sarcosyl through an oligo dT (12-18) cellulose column. After washing, bound RNA was eluted in the same solution without sodium chloride.

EXAMPLE 16

Reverse Transcription of mRNA

Ten micrograms of poly A+ BT-20 RNA were primed for reverse transcription with oligo dT (12-18) and pdN$_6$ primers. One hundred microliter reaction was performed for 4 hours at 42° C. with 200 units of AMV reverse transcriptase (Life Sciences, Inc., St. Petersburg, Fla., U.S.A.). The RNA component of the cDNA/mRNA hybrids was replaced with the second complementary strand by treatment with RNase H, *E. coli* DNA polymerase I and *E. coli* DNA ligase at 12° C. and 22° C. for 1.5 hours each. Molecular ends were polished by treatment with T$_4$ DNA polymerase. cDNA was phenol/chloroform extracted, ethanol precipitated and purified over a "SEPHADEX G-50" spun column prepared in 10 mM Tris-HCl, pH 7.8, 1 mM EDTA (TE).

EXAMPLE 17

Cloning of cBT20

Synthetic DNA linkers

```
5'pCCCGGG      3'
3' GGGCCCTTAA5'
``` were attached to the ends of cDNA by blunt end ligation with excess T$_4$ DNA ligase. Excess linkers were removed by chromatography through "SEPHADEX G-50" (medium) in TE, and by fractionation on 0.8% low melting agarose gel. Based on a Northern blot analysis of poly A+ RNA of the BT-20 cell line, the size of the CEA-related mRNA was estimated at 3.0 kb. Therefore, cDNA fragments between 2 and 4 kb were recovered from gel slices and fragments were ethanol precipitated. After resuspension of cDNA in TE, EcoRI-cleaved lambda gt10 arms were added to cDNA at an estimated molar ratio of 1:1. Ligation proceeded at 7° C. for 2 days in the presence of T4 DNA ligase. Aliquots of the ligation reaction were added to commercially-obtained packaging mix (Stratagene, San Diego, Calif., U.S.A.) for preparation of lambda particles. Five million phage particles were obtained after in vitro packaging and infection of E. coli host NM514.

EXAMPLE 18

Screening of Recombinant Library

Five hundred thousand packaged lambda particles were plated on lawns of E. coli NM514 and replicate patterns were lifted onto nitrocellulose sheets as described by W. D. Benton and R. W. Davis, Science, 196, 180-182, (1977). Positive phage were selected by hybridization with $^{32}$p-labeled LV7 cDNA insert probe that contained a domain repeated among various CEA family members. By this selection method, twenty positive phage were obtained after multiple rounds of screening. Phage from individual plaques were amplified and titered, and these were used to prepare small quantities of recombinant phage DNA.

EXAMPLE 19

DNA Manipulation

Phage DNA was prepared according to T. Maniatis, E. F. Fritsch and J. Sambrook, Molecular Cloning, A Laboratory Manual, Cold Spring Harbor, (1982). DNA segments were isolated from low melting agarose gels and inserted for subcloning into Bluescript plasmid vectors (Stratagene, San Diego, Calif., U.S.A.) DNA sequencing was performed by the dideoxy termination method of F. Sanger, S. Nicklen and A. R. Couslon, Proc. Natl. Acad. Sci., U.S.A., 74, 5463-5467, (1977). One of the abovementioned twenty positive clones (labeled as BT-20) that contained the expected full length sequence for NCA was deposited with the ATCC on May 25, 1988 and given the identification number 67711, and its translated sequence is as follows:

```
         10         20         30         40         50
         |          |          |          |          |
CC GGG GGA CAC GCA GGG CCA ACA GTC ACA GCA GCC CTG ACC AGA GCA TTC CTG GAG CTC 60         70         80         90        100        110
 |          |          |          |          |          |
AAG CTC TCT ACA AAG AGG TGG ACA GAG AAG ACA GCA GAG ACC ATG GGA CCC CCC TCA
                                                     Met Gly Pro Pro Ser 120        130        140        150        160        170
         |          |          |          |          |          |
GCC CCT CCC TGC AGA TTG CAT GTC CCC TGG AAG GAG GTC CTG CTC ACA GCC TCA CTT
Ala Pro Pro Cys Arg Leu His Val Pro Trp Lys Glu Val Leu Leu Thr Ala Ser Leu 180        190        200        210        220        230
         |          |          |          |          |          |
CTA ACC TTC TGG AAC CCA CCC ACC ACT GCC AAG CTC ACT ATT GAA TCC ACG CCA TTC
Leu Thr Phe Trp Asn Pro Pro Thr Thr Ala Lys Leu Thr Ile Glu Ser Thr Pro Phe
                                    1   2   3   4   5   6   7   8   9

240        250        260        270        280
         |          |          |          |          |
AAT GTC GCA GAG GGG AAG GAG GTT CTT CTA CTC GCC CAC AAC CTG CCC CAG AAT CGT
Asn Val Ala Glu Gly Lys Glu Val Leu Leu Leu Ala His Asn Leu Pro Gln Asn Arg
10  11  12  13  14  15  16  17  18  19  20  21  22  23  24  25  26  27  28

290        300        310        320        330        340
         |          |          |          |          |          |
ATT GGT TAC AGC TGG TAC AAA GGC GAA AGA GTG GAT GGC AAC AGT CTA ATT GTA GGA
Ile Gly Tyr Ser Trp Tyr Lys Gly Glu Arg Val Asp Gly Asn Ser Leu Ile Val Gly
29  30  31  32  33  34  35  36  37  38  39  40  41  42  43  44  45  46  47

350        360        370        380        390        400
         |          |          |          |          |          |
TAT GTA ATA GGA ACT CAA CAA GCT ACC CCA GGG CCC GCA TAC AGT GGT CGA GAG ACA
Tyr Val Ile Gly Thr Gln Gln Ala Thr Pro Gly Pro Ala Tyr Ser Gly Arg Glu Thr
48  49  50  51  52  53  54  55  56  57  58  59  60  61  62  63  64  65  66

410        420        430        440        450
         |          |          |          |          |
ATA TAC CCC AAT GCA TCC CTG CTG ATC CAG AAC GTC ACC CAG AAT GAC ACA GGA TTC
Ile Tyr Pro Asn Ala Ser Leu Leu Ile Gln Asn Val Thr Gln Asn Asp Thr Gly Phe
67  68  69  70  71  72  73  74  75  76  77  78  79  80  81  82  83  84  85

460        470        480        490        500        510
         |          |          |          |          |          |
TAC ACC CTA CAA GTC ATA AAG TCA GAT CTT GTG AAT GAA GAA GCA ACC GGA CAG TTC
Tyr Thr Leu Gln Val Ile Lys Ser Asp Leu Val Asn Glu Glu Ala Thr Gly Gln Phe
86  87  88  89  90  91  92  93  94  95  96  97  98  99  100 101 102 103 104

520        530 540               550        560        570
         |          |   |                 |          |          |
CAT GTA TAC CCG GAG CTG CCC AAG CCC TCC ATC TCC AGC AAC AAC TCC AAC CCC GTG
His Val Tyr Pro Glu Leu Pro Lys Pro Ser Ile Ser Ser Asn Asn Ser Asn Pro Val
105 106 107 108 109 110 111 112 113 114 115 116 117 118 119 120 121 122 123
```

-continued

```
              580             590             600             610             620
               |               |               |               |               |
GAG GAC AAG GAT GCT GTG GCC TTC ACC TGT GAA CCT GAG GTT CAG AAC ACA ACC TAC
Glu Asp Lys Asp Ala Val Ala Phe Thr Cys Glu Pro Glu Val Gln Asn Thr Thr Tyr
124 125 126 127 128 129 130 131 132 133 134 135 136 137 138 139 140 141 142

630             640             650             660             670             680
       |               |               |               |               |               |
CTG TGG TGG GTA AAT GGT CAG AGC CTC CCG GTC AGT CCC AGG CTG CAG CTG TCC AAT
Leu Trp Trp Val Asn Gly Gln Ser Leu Pro Val Ser Pro Arg Leu Gln Leu Ser Asn
143 144 145 146 147 148 149 150 151 152 153 154 155 156 157 158 159 160 161

690             700             710             720             730             740
       |               |               |               |               |               |
GGC AAC AGG ACC CTC ACT CTA CTC AGC GTC AAA AGG AAC GAT GCA GGA TCG TAT GAA
Gly Asn Arg Thr Leu Thr Leu Leu Ser Val Lys Arg Asn Asp Ala Gly Ser Tyr Glu
162 163 164 165 166 167 168 169 170 171 172 173 174 175 176 177 178 179 180

750             760             770             780             790             800
              |               |               |               |               |               |
TGT GAA ATA CAG AAC CCA GCG AGT GCC AAC CGC AGT GAC CCA GTC ACC CTG AAT GTC
Cys Glu Ile Gln Asn Pro Ala Ser Ala Asn Arg Ser Asp Pro Val thr Leu Asn Val
181 182 183 184 185 186 187 188 189 190 191 192 193 194 195 196 197 198 199

810             820             830             840             850
              |               |               |               |               |
CTC TAT GGC CCA GAT GGC CCC ACC ATT TCC CCC TCA AAG GCC AAT TAC CGT CCA GGG
Leu Tyr Gly Pro Asp Gly Pro Thr Ile Ser Pro Ser Lys Ala Asn Tyr Arg Pro Gly
200 201 202 203 204 205 206 207 208 209 210 211 212 213 214 215 216 217 218

860             870             880             890             900             910
              |               |               |               |               |               |
GAA AAT CTG AAC CTC TCC TGC CAC GCA GCC TCT AAC CCA CCT GCA CAG TAC TCT TGG
Glu Asn Leu Asn Leu Ser Cys His Ala Ala Ser Asn Pro Pro Ala Gln Tyr Ser Trp
219 220 221 222 223 224 225 226 227 228 229 230 231 232 233 234 235 236 237

920             930             940             950             960             970
              |               |               |               |               |               |
TTT ATC AAT GGG ACG TTC CAG CAA TCC ACA CAA GAG CTC TTT ATC CCC AAC ATC ACT
Phe Ile Asn Gly Thr Phe Gln Gln Ser Thr Gln Glu Leu Phe Ile Pro Asn Ile Thr
238 239 240 241 242 243 244 245 246 247 248 249 250 251 252 253 254 255 256

980             990             1000            1010            1020
       |               |               |               |               |
GTG AAT AAT AGC GGA TCC TAT ATG TGC CAA GCC CAT AAC TCA GCC ACT GGC CTC AAT
Val Asn Asn Ser Gly Ser Tyr Met Cys Gln Ala His Asn Ser Ala Thr Gly Leu Asn
257 258 259 260 261 262 263 264 265 266 267 268 269 270 271 272 273 274 275

1030            1040            1050            1060            1070            1080
       |               |               |               |               |               |
AGG ACC ACA GTC ACG ATG ATC ACA GTC TCT GGA AGT GCT CCT GTC CTC TCA GCT GTG
Arg Thr Thr Val Thr Met Ile Thr Val Ser Gly Ser Ala Pro Val Leu Ser Ala Val
276 277 278 279 280 281 282 283 284 285 286 287 288 289 290 291 292 293 294

1090            1100            1110            1120            1130            1140
       |               |               |               |               |               |
GCC ACC GTC GGC ATC ACG ATT GGA GTG CTG GCC AGG GTG GCT CTG ATA TAG CAG CCC
Ala Thr Val Gly Ile Thr Ile Gly Val Leu Ala Arg Val Ala Leu Ile
295 296 297 298 299 300 301 302 303 304 305 306 307 308 309 310

1150            1160            1170            1180            1190
       |               |               |               |               |
TGG TGT ATT TTC GAT ATT TCA GGA AGA CTG GCA GAT TGG ACC AGA CCC TGA ATT CTT 1200            1210            1220            1230            1240            1250
 |               |               |               |               |               |
CTA GCT CCT CCA ATC CCA TTT TAT CCC ATG GAA CCA CTA AAA ACA AGG TCT GCT CTG 1260            1270            1280            1290            1300            1310
 |               |               |               |               |               |
CTC CTG AAG CCC TAT ATG CTG GAG ATG GAC AAC TCA ATG AAA ATT TAA AGG AAA AAC 1320            1330            1340            1350            1360            1370
       |               |               |               |               |               |
CCT CAG GCC TGA GGT GTG TGC CAC TCA GAG ACT TCA CCT AAC TAG AGA CAG GCA AAC 1380            1390            1400            1410            1420
              |               |               |               |               |
TGC AAA CCA nnC CTC TTT CGC TTG GCA GGA TGA TGG TGT CAT TAG TAT TTC ACA AGA 1430            1440            1450            1460            1470            1480
 |               |               |               |               |               |
AGT AGC TTC AGA GGG TAA CTT AAC AGA GTA TCA GAT CTA TCT TGT CAA TCC AAC GT 1490            1500            1510            1520            1530            1540
       |               |               |               |               |               |
TTT ACA TAA AAT AAG CGA TCC TTT AGT GCA CCC AGT GAC TGA CAT TAG CAG CAT CTT
```

-continued

```
        1550         1560         1570         1580         1590
         |            |            |            |            |
TAA CAC AGC CGT GTG TTC AAG TGT ACA GTG GTC CTT TTC AGA GTT GGn nnT ACT CCA 1600         1610         1620         1630         1640         1650
     |            |            |            |            |            |
ACT GAA ATG TTA AGG AAG AAG ATA GAT CCA ATT AAA AAA AAT TAA AAC CAA TTT AAA 1660         1670         1680         1690         1700         1710
     |            |            |            |            |            |
AAA AAA AAA GAA CAC AGG AGA TTC CAG TCT ACT TGA GTT AGC ATA ATA CAG AAG TCC 1720         1730         1740         1750         1760
         |            |            |            |            |
CCT CTA CTT TAA CTT TTA CAA AAA AGT AAC CTG AAC TAA TCT GAT GTT AAC CAA TGT 1770         1780         1790         1800         1810         1820
     |            |            |            |            |            |
ATT TAT TTG TCT GGT TCT GTT TCC TTG TTC CAA TTT GAC AAA ACC CAC TGT TCT TGT 1830         1840         1850         1860         1870         1880
         |            |            |            |            |            |
ATT GTA TTG CCC AGG GGG AGC TAT CAC TGT ACT TGT AGA GTG GTG CTG CTT TAA GTT 1890         1900         1910         1920         1930         1940
     |            |            |            |            |            |
CAT AAA TCA CAA ATA AAA GCC AAT TAG CTC TAT AAC TAA AAA AAA AAA AAA AAA AAA 1950         1960
         |            |
AAA AAA AAA AAA AAA AAA AAA AAA
```

Note: the "nn" at positions 1380-1381 and the "nnn" at positions 1589-1591 represent, as yet, unsequenced regions of the 3'-translated region of cBT-20.

For residue sequence purposes, the first amino acid is Lys in row four, 11 amino acids from the left. Thereafter the amino acids are numbered consecutively.

It will be appreciated that the instant specification and claims are set forth by way of illustration and not limitation, and that various modifications and changes may be made without departing from the spirit and scope of the present invention.

What is claimed is:

1. An isolated nucleic acid which codes for a polypeptide belonging to the CEA family, said isolated nucleic acid having the following nucleotide sequence:

```
GGGGTTTACA CAACCACCAC CCCATCAAAC                 40
                                  CCTTCATCAC
CAGCAACAAC TCCAACCCCG TGGAGGATGA                 80
                                  GGATGCTGTA
GCCTTAACCT GTGAACCTCA GATTCAGAAC                120
                                  ACAACCTACC
TGTGGTGGGT AAATAATCAG AGCCTCCCGG                160
                                  TCAGTCCCAG
GCTGCAGCTG TCCAATGACA ACAGGACCCT                200
                                  CACTCTACTC
AGTGTCACAA GGAATGATGT AGGACCCTAT                240
                                  GAGTGTGGAA
TCCAGAACGA ATTAAGTGTT GACCACAGCG                280
                                  ACCCAGTCAT
CCTGAATGTC CTCTATGGCC CAGACGACCC                320
                                  CACCATTTCC
CCCTCATACA CCTATTACCG TCCAGGGGTG                360
                                  AACCTCAGCC
TCTCCTGCCA TGCAGCCTCT AACCCACCTG                400
                                  CACAGTATTC
TTGGCTGATT GATGGGAACA TCCAGCAACA                440
                                  CACACAAGAG
CTCTTTATCT CCAACATCAC TGAGAAGAAC                480
                                  AGCGGACTCT
ATACCTGCCA GGCCAATAAC TCAGCCAGTG                520
                                  GCCACAGCAG
GACTACAGTC AAGACAATCA CAGTCTCTGC                560
                                  GGACGTGCCC
AAGCCCTCCA TCTCCAGCAA CAACTCCAAA                600
                                  CCCGTGGAGG
ACAAGGATGC TGTGGCCTTC CACTGTGAAC                640
                                  CTGAGGCTCA
GAACACAACC TACCTGTGGT GGGTAAATGG                680
                                  TCAGAGCCTC
CCAGTCAGTC CCAGGCTGCA GCTGTCCAAT                720
                                  GGCAACAGGA
CCCTCACTCT ATTCAATGTC ACAAGAAATG                760
                                  ACGCAAGAGC
CTATGTATGT GGAATCCAGA ACTCAGTGAG                800
                                  TGCAAACCGC
AGTGACCCAG TCACCCTGGA TGTCCTCTAT                840
                                  GGGCCGGACA
CCCCCATCAT TTCCCCCCCC CC                        862.
```

2. An isolated nucleic acid which codes for a polypeptide belonging to the CEA family, said isolated nucleic acid having the following nucleotide sequence:

```
CACC ATG GAG TCT CCC TCG GCC CCT CTC CAC AGA TGG TGC    40
ATC CCC TGG CAG AGG CTC CTG CTC ACA GCC TCA CTT CTA    79
ACC TTC TGG AAC CCG CCC ACC ACT GCC AAG CTC ACT ATT   118
GAA TCC ACG CCG TTC AAT GTC GCA GAG GGG AAG GAG GTG   157
CTT CTA CTT GTC CAC AAT CTG CCC CAG CAT CTT TTT GGC   196
TAC AGC TGG TAC AAA GGT GAA AGA GTG GAT GGC AAC CGT   235
CAA ATT ATA GGA TAT GTA ATA GGA ACT CAA CAA GCT ACC   274
```

| | | | | | | | | | | | | |
|---|---|---|---|---|---|---|---|---|---|---|---|---|
| CCA | GGG | CCC | GCA | TAC | AGT | GGT | CGA | GAG | ATA | ATA | TAC | CCC | 313 |
| AAT | GCA | TCC | CTG | CTG | ATC | CAG | AAC | ATC | ATC | CAG | AAT | GAC | 352 |
| ACA | GGA | TTC | TAC | ACC | CTA | CAC | GTC | ATA | AAG | TCA | GAT | CTT | 391 |
| GTG | AAT | GAA | GAA | GCA | ACT | GGC | CAG | TTC | CGG | GTA | TAC | CCG | 430 |
| GAG | CTG | CCC | AAG | CCC | TCC | ATC | TCC | AGC | AAC | AAC | TCC | AAA | 469 |
| CCC | GTG | GAG | GAC | AAG | GAT | GCT | GTG | GCC | TTC | ACC | TGT | GAA | 508 |
| CCT | GAG | ACT | CAG | GAC | GCA | ACC | TAC | CTG | TGG | TGG | GTA | AAC | 547 |
| AAT | CAG | AGC | CTC | CCG | GTC | AGT | CCC | AGG | CTG | CAG | CTG | TCC | 586 |
| AAT | GGC | AAC | AGG | ACC | CTC | ACT | CTA | TTC | AAT | GTC | ACA | AGA | 625 |
| AAT | GAA | CAA | GCA | AGC | TAC | AAA | TGT | GAA | ACC | CAG | AAC | CCA | 664 |
| GTG | AGT | GCC | AGG | CGC | AGT | GAT | TCA | GTC | ATC | CTG | AAT | GTC | 703 |
| CTC | TAT | GGC | CCG | GAT | GCC | CCC | ACC | ATT | TCC | CCT | CTA | AAC | 742 |
| ACA | TCT | TAC | AGA | TCA | GGG | GAA | AAT | CTG | AAC | CTC | TCC | TGC | 781 |
| CAC | GCA | GCC | TCT | AAC | CCA | CCT | GCA | CAG | TAC | TCT | TGG | TTT | 820 |
| GTC | AAT | GGG | ACT | TTC | CAG | CAA | TCC | ACC | CAA | GAG | CTC | TTT | 859 |
| ATC | CCC | AAC | ATC | ACT | GTG | AAT | AAT | AGT | GGA | TCC | TAT | ACG | 898 |
| TGC | CAA | GCC | CAT | AAC | TCA | GAC | ACT | GGC | CTC | AAT | AGG | ACC | 937 |
| ACA | GTC | ACG | ACG | ATC | ACA | GTC | TAT | GCA | GAG | CCA | CCC | AAA | 976 |
| CCC | TTC | ATC | ACC | AGC | AAC | AAC | TCC | AAC | CCC | GTG | GAG | GAT | 1015 |
| GAG | GAT | GCT | GTA | GCC | TTA | ACC | TGT | GAA | CCT | GAG | ATT | CAG | 1054 |
| AAC | ACA | ACC | TAC | CTG | TGG | TGG | GTA | AAT | AAT | CAG | AGC | CTC | 1093 |
| CCG | GTC | AGT | CCC | AGG | CTG | CAG | CTG | TCC | AAT | GAC | AAC | AGG | 1132 |
| ACC | CTC | ACT | CTA | CTC | AGT | GTC | ACA | AGG | AAT | GAT | GTA | GGA | 1171 |
| CCC | TAT | GAG | TGT | GGA | ATC | CAG | AAC | GAA | TTA | AGT | GTT | GAC | 1210 |
| CAC | AGC | GAC | CCA | GTC | ATC | CTG | AAT | GTC | CTC | TAT | GGC | CCA | 1249 |
| GAC | GAC | CCC | ACC | ATT | TCC | CCC | TCA | TAC | ACC | TAT | TAC | CGT | 1288 |
| CCA | GGG | GTG | AAC | CTC | AGC | CTC | TCC | TGC | CAT | GCA | GCC | TCT | 1327 |
| AAC | CCA | CCT | GCA | CAG | TAT | TCT | TGG | CTG | ATT | GAT | GGG | AAC | 1366 |
| ATC | CAG | CAA | CAC | ACA | CAA | GAG | CTC | TTT | ATC | TCC | ACC | ATC | 1405 |
| ACT | GAG | AAG | AAC | AGC | GGA | CTC | TAT | ACC | TGC | CAG | GCC | AAT | 1444 |
| AAC | TCA | GCC | AGT | GGC | CAC | AGC | AGG | ACT | ACA | GTC | AAG | ACA | 1483 |
| ATC | ACA | GTC | TCT | GCG | GAC | GTG | CCC | AAG | CCC | TCC | ATC | TCC | 1522 |
| AGC | AAC | AAC | TCC | AAA | CCC | GTG | GAG | GAC | AAG | GAT | GCT | GTG | 1561 |
| GCC | TTC | ACC | TGT | GAA | CCT | GAG | GCT | CAG | AAC | ACA | ACC | TAC | 1600 |
| CTG | TGG | TGG | GTA | AAT | GGT | CAG | AGC | CTC | CCA | GTC | AGT | CCC | 1639 |
| AGG | CTG | CAG | CTG | TCC | AAT | GGC | AAC | AGG | ACC | CTC | ACT | CTA | 1678 |
| TTC | AAT | GTC | ACA | AGA | AAT | GAC | GCA | AGA | GCC | TAT | GTA | TGT | 1717 |
| GGA | ATC | CAG | AAC | TCA | GTG | AGT | GCA | AAC | CGC | AGT | GAC | CCA | 1756 |
| GTC | ACC | CTG | GAT | GTC | CTC | TAT | GGG | CCG | GAC | ACC | CCC | ATC | 1795 |
| ATT | TCC | CCC | CCA | GAC | TCG | TCT | TAC | CTT | TCG | GGA | GCG | AAC | 1834 |
| CTC | AAC | CTC | TCC | TGC | CAC | TCG | GCC | TCT | AAC | CCA | TCC | CCG | 1873 |

-continued

| | | | | | | | | | | | | |
|---|---|---|---|---|---|---|---|---|---|---|---|---|
| CAG | TAT | TCT | TGG | CGT | ATC | AAT | GGG | ATA | CCG | CAG | CAA | CAC | 1912 |
| ACA | CAA | GTT | CTC | TTT | ATC | GCC | AAA | ATC | ACG | CCA | AAT | AAT | 1951 |
| AAC | GGG | ACC | TAT | GCC | TGT | TTT | GTC | TCT | AAC | TTG | GCT | ACT | 1990 |
| GGC | CGC | AAT | AAT | TCC | ATA | GTC | AAG | AGC | ATC | ACA | GTC | TCT | 2029 |
| GCA | TCT | GGA | ACT | TCT | CCT | GGT | CTC | TCA | GCT | GGG | GCC | ACT | 2068 |
| GTC | GGC | ATC | ATG | ATT | GGA | GTG | CTG | GTT | GGG | GTT | GCT | CTG | 2107 |

| | | | |
|---|---|---|---|
| ATA TAGCAGCCCT | GGTGAGTTT | CTTCATTTCA | GGAAGACTGA | 2150 |
| CAGTTGTTTT | GCTTCTTCCT | TAAAGCATTT | GCAACAGCTA | 2190 |
| CAGTCTAAAA | TTGCTTCTTT | ACCAAGGATA | TTTACAGAAA | 2230 |
| ATACTCTGAC | CAGAGATCGA | GACCATCCTA | GCCAACATCG | 2270 |
| TGAAACCCCA | TCTCTACTAA | AAATACAAAA | ATGAGCTGGG | 2310 |
| CTTGGTGGCG | CGCACCTGTA | GTCCCAGTTA | CTCGGGAGGC | 2350 |
| TGAGGCAGGA | GAATCGCTTG | AACCCGGGAG | GTGGAGATTG | 2390 |
| CAGTGAGCCC | AGATCGCACC | ACTGCACTCC | AGTCTGGCAA | 2430 |
| CAGAGCAAGA | CTCCATCTCA | AAAAGAAAAG | AAAAGAAGAC | 2470 |
| TCTGACCTGT | ACTCTTGAAT | ACAAGTTTCT | GATACCACTG | 2510 |
| CACTGTCTGA | GAATTTCCAA | AACTTTAATG | AACTAACTGA | 2550 |
| CAGCTTCATG | AAACTGTCCA | CCAAGATCAA | GCAGAGAAAA | 2590 |
| TAATTAATTT | CATGGGGACT | AAATGAACTA | ATGAGGATAA | 2630 |
| TATTTTCATA | ATTTTTTATT | TGAAATTTTG | CTGATTCTTT | 2670 |
| AAATGTCTTG | TTTCCCAGAT | TTCAGGAAAC | TTTTTTTCTT | 2710 |
| TTAAGCTATC | CACTCTTACA | GCAATTTGAT | AAAATATACT | 2750 |
| TTTGTAACA | AAAATTGAGA | CATTTACATT | TTATCCCTAT | 2790 |
| GTGGTCGCTC | CAGACTTGGG | AAACTATTCA | TGAATATTTA | 2830 |
| TAT | TGT | ATG | | 2839. |

3. An isolated nucleic acid which codes for a polypeptide belonging to the CEA family, said isolated nucleic acid having the following nucleotide sequence:

| | | | |
|---|---|---|---|
| CAGCCGTGCT | CGAAGCGTTC | CTGGAGCCCA | AGCTCTCCTC | 40 |
| CACAGGTGAA | GACAGGGCCA | GCAGGAGACA | CC ATG GGG | 78 |

| | | | | | | | | | | | | |
|---|---|---|---|---|---|---|---|---|---|---|---|---|
| CAC | CTC | TCA | GCC | CCA | CTT | CAC | AGA | GTC | CGT | GTA | CCC | TGG | 117 |
| CAG | GGG | CTT | CTG | CTC | ACA | GCC | TCA | CTT | CTA | ACC | TTC | TGG | 156 |
| AAC | CCG | CCC | ACC | ACT | GCC | CAG | CTC | ACT | ACT | GAA | TCC | ATG | 195 |
| CCA | TTC | AAT | GTT | GCA | GAG | GGG | AAG | GAG | GTT | CTT | CTC | CTT | 234 |
| GTC | CAC | AAT | CTG | CCC | CAG | CAA | CTT | TTT | GGC | TAC | AGC | TGG | 273 |
| TAC | AAA | GGG | GAA | AGA | GTG | GAT | GGC | AAC | CGT | CAA | ATT | GTA | 312 |
| GGA | TAT | GCA | ATA | GGA | ACT | CAA | CAA | GCT | ACC | CCA | GGG | CCC | 351 |
| GCA | AAC | AGC | GGT | CGA | GAG | ACA | ATA | TAC | CCC | AAT | GCA | TCC | 390 |
| CTG | CTG | ATC | CAG | AAC | GTC | ACC | CAG | AAT | GAC | ACA | GGA | TTC | 429 |
| TAC | ACC | CTA | CAA | GTC | ATA | AAG | TCA | GAT | CTT | GTG | AAT | GAA | 468 |
| GAA | GCA | ACT | GGA | CAG | TTC | CAT | GTA | TAC | CCG | GAG | CTG | CCC | 507 |
| AAG | CCC | TCC | ATC | TCC | AGC | AAC | AAC | TCC | ACC | CCT | GTG | GAG | 546 |

| | | | | | | | | | | | | |
|---|---|---|---|---|---|---|---|---|---|---|---|---|
| GAC | AAG | GAT | GCT | GTG | GCC | TTC | ACC | TGT | GAA | CCT | GAG | ACT | 585 |
| CAG | GAC | ACA | ACC | TAC | CTG | TGG | TGG | ATA | AAC | AAT | CAG | AGC | 624 |
| CTC | CCG | GTC | AGT | CCC | AGG | CTG | CAG | CTG | TCC | AAT | GGC | AAC | 663 |
| AGG | ACC | CTC | ACT | CTA | CTC | AGT | GTC | ACA | AGG | AAT | GAC | ACA | 702 |
| GGA | CCC | TAT | GAG | TGT | GAA | ATA | CAG | AAC | CCA | GTG | AGT | GCG | 741 |
| AAC | CGC | AGT | GAC | CCA | GTC | ACC | TTG | AAT | GTC | ACC | TAT | GGC | 780 |
| CCG | GAC | ACC | CCC | ACC | ATT | TCC | CCT | TCA | GAC | ACC | TAT | TAC | 819 |
| CGT | CCA | GGG | GCA | AAC | CTC | AGC | CTC | TCC | TGC | TAT | GCA | GCC | 858 |
| TCT | AAC | CCA | CCT | GCA | CAG | TAC | TCC | TGG | CTT | ATC | AAT | GGA | 897 |
| ACA | TTC | CAG | CAA | AGC | ACA | CAA | GAG | CTC | TTT | ATC | CCT | AAC | 936 |
| ATC | ACT | GTG | AAT | AAT | AGT | GGA | TCC | TAT | ACC | TGC | CAC | GCC | 975 |
| AAT | AAC | TCA | GTC | ACT | GGC | TGC | AAC | AGG | ACC | ACA | GTC | AAG | 1014 |
| ACG | ATC | ATA | GTC | ACT | GAG | CTA | AGT | CCA | GTA | GTA | GCA | AAG | 1053 |
| CCC | CAA | ATC | AAA | GCC | AGC | AAG | ACC | ACA | GTC | ACA | GGA | GAT | 1092 |
| AAG | GAC | TCT | GTG | AAC | CTG | ACC | TGC | TCC | ACA | AAT | GAC | ACT | 1131 |
| GGA | ATC | TCC | ATC | CGT | TGG | TTC | TTC | AAA | AAC | CAG | AGT | CTC | 1170 |
| CCG | TCC | TCG | GAG | AGG | ATG | AAG | CTG | TCC | CAG | GGC | AAC | ACC | 1209 |
| ACC | CTC | AGC | ATA | AAC | CCT | GTC | AAG | AGG | GAG | GAT | GCT | GGG | 1248 |
| ACG | TAT | TGG | TGT | GAG | GTC | TTC | AAC | CCA | ATC | AGT | AAG | AAC | 1287 |
| CAA | AGC | GAC | CCC | ATC | ATG | CTG | AAC | GTA | AAC | TAT | AAT | GCT | 1326 |
| CTA | CCA | CAA | GAA | AAT | GGC | CTC | TCA | CCT | GGG | GCC | ATT | GCT | 1365 |
| GGC | ATT | GTG | ATT | GGA | GTA | GTG | GCC | CTG | GTT | GCT | CTG | ATA | 1404 |
| GCA | GTA | GCC | CTG | GCA | TGT | TTT | CTG | CAT | TTC | GGG | AAG | ACC | 1443 |
| GGC | AGG | GCA | AGC | GAC | CAG | CGT | GAT | CTC | ACA | GAG | CAC | AAA | 1482 |
| CCC | TCA | GTC | TCC | AAC | CAC | ACT | CAG | GAC | CAC | TCC | AAT | GAC | 1521 |
| CCA | CCT | AAC | AAG | ATG | AAT | GAA | GTT | ACT | TAT | TCT | ACC | CTG | 1560 |
| AAC | TTT | GAA | GCC | CAG | CAA | CCC | ACA | CAA | CCA | ACT | TCA | GCC | 1599 |
| TCC | CCA | TCC | CTA | ACA | GCC | ACA | GAA | ATA | ATT | TAT | TCA | GAA | 1638 |

| | | | |
|---|---|---|---|
| GTA AAA AAG CAG | TAATGAAACC | TGTCCTGCTC | ACTGCAGTGC | 1680 |
| TGATGTATTT | CAAGTCTCTC | ACCCTCATCA | CTAGGAGATT | 1720 |
| CCTTTCCCCT | GTAGGGTAGA | GGGGTGGGGA | CAGAAACAAC | 1760 |
| TTTCTCCTAC | TCTTCCTTCC | TAATAGGCAT | CTCCAGGCTG | 1800 |
| CCTGGTCACT | GCCCCTCTCT | CAGTGTCAAT | AGATGAAAGT | 1840 |
| ACATTGGGAG | TCTGTAGGAA | ACCCAACCTT | CTTGTCATTG | 1880 |
| AAATTTGGCA | AAGCTGACTT | TGGGAAGAG | GGACCAGAAC | 1920 |
| TTCCCCTCCC | TTCCCCTTTT | CCCAACCTGG | ACTTGTTTTA | 1960 |
| AACTTGCCTG | TTCAGAGCAC | TCATTCCTTC | CCACCCCCAG | 2000 |
| TCCTGTCCTA | TCACTCTAAT | TCGGATTTGC | CATAGCCTTG | 2040 |
| AGGTAATGTC | CTTTTCCATT | AAGTACATGT | GCCAGGAAAC | 2080 |
| AGCGAGAGAG | AGAAAGTAAA | CGGCAGTAAT | GCTTCTCCTA | 2120 |
| TTTCTCCAAA | GCCTTGTGTG | AACTAGCAAA | GAGAAGAAAA | 2160 |

| | | -continued | | |
|---|---|---|---|---|
| TCAAATATAT | AACAATAGT | GAAATGCCAC | AGGTTTGTCC | 2200 |
| ACTGTCAGGG | TTGTCTACCT | GTAGGATCAG | GGTCTAAGCA | 2240 |
| CCTTGGTGCT | TAGCTAGAAT | ACCACCTAAT | CCTTCTGGCA | 2280 |
| AGCCTGTCTT | CAGAGAACCC | ACTAGAAGCA | ACTAGGAAAA | 2320 |
| ATCACTTGCC | AAAATCCAAG | GCAATTCCTG | ATGGAAAATG | 2360 |
| CAAAAGCACA | TATATGTTTT | AATATCTTTA | TGGGCTCTGT | 2400 |
| TCAAGGCAGT | GCTGAGAGGG | AGGGGTTATA | GCTTCAGGAG | 2440 |
| GGAACCAGCT | TCTGATAAAC | ACAATCTGCT | AGGAACTTGG | 2480 |
| GAAAGGAAT | CAGAGAGCTGC | CCTTCAGCGA | TTATTTAAAT | 2520 |
| TGTTAAAGAA | TACACAATTT | GGGGTATTGG | GATTTTTCTC | 2560 |
| CTTTTCTCTG | AGACATTCCA | CCATTTTAAT | TTTTGTAACT | 2600 |
| GCTTATTTAT | GTGAAAGGG | TTATTTTTAC | TTAGCTTAGC | 2640 |
| TATGTCAGCC | AATCCGATTG | CCTTAGGTGA | AAGAAACCAC | 2680 |
| CGAAATCCCT | CAGGTCCCTT | GGTCAGGAGC | CTCTCAAGAT | 2720 |
| TTTTTTTGTC | AGAGGCTCCA | AATAGAAAAT | AAGAAAAGGT | 2760 |
| TTTCTTCATT | CATGGCTAGA | GCTAGATTTA | ACTCAGTTTC | 2800 |
| TAGGCACCTC | AGACCAATCA | TCAACTACCA | TTCTATTCCA | 2840 |
| TGTTTGCACC | TGTGCATTTT | CTGTTTGCCC | CCATTCACTT | 2880 |
| TGTCAGGAAA | CCTTGGCCTC | TGCTAAGGTG | TATTTGGTCC | 2920 |
| TTGAGAAGTG | GGAGCACCCT | ACAGGGACAC | TATCACTCAT | 2960 |
| GCTGGTGGCA | TTGTTTACAG | CTAGAAAGCT | GCACTGGTGC | 3000 |
| TAATGCCCCT | TGGGAAATGG | GGCTGTGAGG | AGGAGGATTA | 3040 |
| TAACTTAGGC | CTAGCCTCTT | TTAACAGCCT | CTGAAATTTA | 3080 |
| TCTTTTCTTC | TATGGGGTCT | ATAAATGTAT | CTTATAATAA | 3120 |
| AAAGGAAGGA | CAGGAGGAAG | ACAGGCAAAT | GTACTTCTCA | 3160 |
| CCCAGTCTTC | TACACAGATG | GAATCTCTTT | GGGGCTAAGA | 3200 |
| GAAAGGTTTT | ATTCTATATT | GCTTACCTGA | TCTCATGTTA | 3240 |
| GGCCTAAGAG | GCTTTCTCCA | GGAGGATTAG | CTTGGAGTTC | 3280 |
| TCTATACTCA | GGTACCTCTT | TCAGGGTTTT | CTAACCCTGA | 3320 |
| CACGGACTGT | GCATACTTTC | CCTCATCCAT | GCTGTGCTGT | 3360 |
| GTTATTTAAT | TTTTCCTGGC | TAAGATCATG | TCTGAATTAT | 3400 |
| GTATGAAAAT | TATTCTATGT | TTTTATAATA | AAAATAATAT | 3440 |
| ATCAGACATC | GAAAAAAAA | A | | 3461. |

4. An isolated nucleic acid which codes for a polypeptide belonging to the CEA family, said isolated nucleic acid having the following nucleotide sequence:

| CCGGGGGACA | | | CGCAGGGCCA | | | ACAGTCACG | | | CAGCCCTGAC | | | 40 |
|---|---|---|---|---|---|---|---|---|---|---|---|---|
| CAGAGCATTC | | | CTGGAGCTCA | | | AGCTCTCTAC | | | AAAGAGGTGG | | | 80 |
| ACAGAGAAGA | | | CAGCAGAGAC | | | C | ATG | GGA | CCC | CCC | TCA | GCC | 119 |
| CCT | CCC | TGC | AGA | TTG | CAT | GTC | CCC | TGG | AAG | GAG | GTC | CTG | 158 |
| CTC | ACA | GCC | TCA | CTT | CTA | ACC | TTC | TGG | AAC | CCA | CCC | ACC | 197 |
| ACT | GCC | AAG | CTC | ACT | ATT | GAA | TCC | ACG | CCA | TTC | AAT | GTC | 236 |
| GCA | GAG | GGG | AAG | GAG | GTT | CTT | CTA | CTC | GCC | CAC | AAC | CTG | 275 |
| CCC | CAG | AAT | CGT | ATT | GGT | TAC | AGC | TGG | TAC | AAA | GGC | GAA | 314 |
| AGA | GTG | GAT | GGC | AAC | AGT | CTA | ATT | GTA | GGA | TAT | GTA | ATA | 353 |
| GGA | ACT | CAA | CAA | GCT | ACC | CCA | GGG | CCC | GCA | TAC | AGT | GGT | 392 |
| CGA | GAG | ACA | ATA | TAC | CCC | AAT | GCA | TCC | CTG | CTG | ATC | CAG | 431 |

```
                                              -continued
AAC  GTC  ACC  CAG  AAT  GAC  ACA  GGA  TTC  TAC  ACC  CTA  CAA   470
GTC  ATA  AAG  TCA  GAT  CTT  GTG  AAT  GAA  GAA  GCA  ACC  GGA   509
CAG  TTC  CAT  GTA  TAC  CCG  GAG  CTG  CCC  AAG  CCC  TCC  ATC   548
TCC  AGC  AAC  AAC  TCC  AAC  CCC  GTG  GAG  GAC  AAG  GAT  GCT   587
GTG  GCC  TTC  ACC  TGT  GAA  CCT  GAG  GTT  CAG  AAC  ACA  ACC   626
TAC  CTG  TGG  TGG  GTA  AAT  GGT  CAG  AGC  CTC  CCG  GTC  AGT   665
CCC  AGG  CTG  CAG  CTG  TCC  AAT  GGC  AAC  AGG  ACC  CTC  ACT   704
CTA  CTC  AGC  GTC  AAA  AGG  AAC  GAT  GCA  GGA  TCG  TAT  GAA   743
TGT  GAA  ATA  CAG  AAC  CCA  GCG  AGT  GCC  AAC  CGC  AGT  GAC   782
CCA  GTC  ACC  CTG  AAT  GTC  CTC  TAT  GGC  CCA  GAT  GGC  CCC   821
ACC  ATT  TCC  CCC  TCA  AAG  GCC  AAT  TAC  CGT  CCA  GGG  GAA   860
AAT  CTG  AAC  CTC  TCC  TGC  CAC  GCA  GCC  TCT  AAC  CCA  CCT   899
GCA  CAG  TAC  TCT  TGG  TTT  ATC  AAT  GGG  ACG  TTC  CAG  CAA   938
TCC  ACA  CAA  GAG  CTC  TTT  ATC  CCC  AAC  ATC  ACT  GTG  AAT   977
AAT  AGC  GGA  TCC  TAT  ATG  TGC  CAA  GCC  CAT  AAC  TCA  GCC  1016
ACT  GGC  CTC  AAT  AGG  ACC  ACA  GTC  ACG  ATG  ATC  ACA  GTC  1055
TCT  GGA  AGT  GCT  CCT  GTC  CTC  TCA  GCT  GTG  GCC  ACC  GTC  1094
GGC  ATC  ACG  ATT  GGA  GTG  CTG  GCC  AGG  GTG  GCT  CTG  ATA  1133
TAGCAGC         CCTGGTGTAT       TTTCGATATT       TCAGAAGAC      1170
TGGCAGATTG      GACCAGACCC       TGAATTCTTC       TAGCTCCTCC     1210
AATCCCATTT      TATCCCATGG       AACCACTAAA       AACAAGGTCT     1250
GCTCTGCTCC      TGAAGCCCTA       TATGCTGGAG       ATGGACAACT     1290
CAATGAAAAT      TTAAAGGAAA       AACCCTCAGC       CCTGAGGTGT     1330
GTGCCACTCA      GAGACTTCAC       CTAACTAGAG       ACAGGCAAAC     1370
TGCAAACCAn      nCCTCTTTCG       CTTGGCAGGA       TGATGGTGTC     1410
ATTAGTATTT      CACAAGAAGT       AGCTTCAGAG       GGTAACTTAA     1450
CAGAGTATCA      GATCTATCTT       GTCAATCCCA       ACGTTTTACA     1490
TAAAATAAGC      GATCCTTTAG       TGCACCCAGT       GAGTGACATT     1530
AGCAGCATCT      TTAACACAGC       CGTGTGTTCA       AGTGTACAGT     1570
GGTCCTTTTC      AGAGTTGGnn       nTACTCCAAC       TGAAATGTTA     1610
AGGAAGAAGA      TAGATCCAAT       TAAAAAAAAT       TAAAACCAAT     1650
TTAAAAAAAA      AAAAGAACAC       AGGAGATTCC       AGTCTACTTG     1690
AGTTAGCATA      ATACAGAAGT       CCCCTCTACT       TTAACTTTTA     1730
CAAAAAAGTA      ACCTGAACTA       ATCTGATGTT       AACCAATGTA     1770
TTTATTTGTC      TGGTTCTGTT       TCCTTGTTCC       AATTTGACAA     1810
AACCCACTGT      TCTTGTATTG       TATTGCCCAG       GGGGAGCTAT    ·1850
CAC  TGTACTT    GTAGAGTGGT       GCTGCTTTAA       GTTCATAAAT     1890
CACAAATAAA      AGCCAATTAG       CTCTATAACT       AAAAAAAAAA     1930
AAAAAAAAAA      AAAAAAAAAA       AAAAAAAAAA       AAAA           1964.
```

5. The plasmid cloning vector contained in *E. coli* strain ATCC 67312.

6. The plasmid cloning vector contained in *E. coli* strain ATCC 67169.

7. The plasmid cloning vector contained in *E. coli* strain ATCC 67710.

8. The plasmid cloning vector contained in *E. coli* strain ATCC 67711.

* * * * *